United States Patent
Wang et al.

(10) Patent No.: US 9,347,077 B2
(45) Date of Patent: May 24, 2016

(54) OVER-EXPRESSION OF A PUTATIVE OXIDOREDUCTASE (UCPA) FOR INCREASING FURFURAL OR 5-HYDROXYMETHYLFURFURAL TOLERANCE

(75) Inventors: Xuan Wang, Tempe, AZ (US); Elliot N. Miller, Indianapolis, IN (US); Lorraine P. Yomano, Gainesville, FL (US); Keelnatham T. Shanmugam, Gainesville, FL (US); Lonnie O'Neal Ingram, Gainesville, FL (US)

(73) Assignee: UNIVERSITY OF FLORIDA RESEARCH FOUNDATION, INCORPORATED, Gainesville, FL (US)

( * ) Notice: Subject to any disclaimer, the term of this patent is extended or adjusted under 35 U.S.C. 154(b) by 61 days.

(21) Appl. No.: 14/131,468

(22) PCT Filed: Jul. 9, 2012

(86) PCT No.: PCT/US2012/045912
§ 371 (c)(1),
(2), (4) Date: Jan. 8, 2014

(87) PCT Pub. No.: WO2013/009679
PCT Pub. Date: Jan. 17, 2013

(65) Prior Publication Data
US 2014/0212933 A1 Jul. 31, 2014

Related U.S. Application Data

(60) Provisional application No. 61/505,684, filed on Jul. 8, 2011.

(51) Int. Cl.
| | |
|---|---|
| C12P 13/00 | (2006.01) |
| C12P 7/56 | (2006.01) |
| C12P 7/46 | (2006.01) |
| C12P 7/10 | (2006.01) |
| C07K 14/245 | (2006.01) |
| C12N 9/02 | (2006.01) |
| C12P 7/06 | (2006.01) |
| C12P 7/16 | (2006.01) |
| C12P 7/18 | (2006.01) |
| C12P 7/40 | (2006.01) |
| C12P 7/44 | (2006.01) |
| C12P 7/54 | (2006.01) |

(52) U.S. Cl.
CPC ............ *C12P 13/001* (2013.01); *C07K 14/245* (2013.01); *C12N 9/0004* (2013.01); *C12P 7/06* (2013.01); *C12P 7/065* (2013.01); *C12P 7/10* (2013.01); *C12P 7/16* (2013.01); *C12P 7/18* (2013.01); *C12P 7/40* (2013.01); *C12P 7/44* (2013.01); *C12P 7/46* (2013.01); *C12P 7/54* (2013.01); *C12P 7/56* (2013.01); *C12P 2203/00* (2013.01); *Y02E 50/16* (2013.01); *Y02E 50/17* (2013.01); *Y02P 20/52* (2015.11)

(58) Field of Classification Search
None
See application file for complete search history.

(56) References Cited

U.S. PATENT DOCUMENTS

| | | |
|---|---|---|
| 2007/0037265 A1 | 2/2007 | Zhou et al. |
| 2008/0090283 A1 | 4/2008 | Lefebvre et al. |
| 2009/0148914 A1 | 6/2009 | Causey et al. |
| 2010/0184171 A1 | 7/2010 | Jantama et al. |
| 2014/0024086 A1 | 1/2014 | Miller et al. |

FOREIGN PATENT DOCUMENTS

| | | |
|---|---|---|
| WO | WO 2008/116851 | 10/2008 |
| WO | WO 2010/115067 | 7/2010 |
| WO | WO 2010/101665 | 9/2010 |
| WO | WO 2012/135420 | 10/2012 |

OTHER PUBLICATIONS

Wang et al. Appl Environ Microbiol. Aug. 2011;77(15):5132-40. Epub Jun. 17, 2011.*
Chica et al. Curr Opin Biotechnol. Aug. 2005;16(4):378-84.*
Sen et al. Appl Biochem Biotechnol. Dec. 2007;143(3):212-23.*
Accession P37440. Oct. 1, 1994.*
Almeida, J.R., et al., "Metabolic effects of furaldehydes and impacts on biotechnological processes", *Applied Microbiology and Biotechnology*, 2009, vol. 82, pp. 625-638.
Almeida, J.R., et al., "NADH- vs NADPH-coupled reduction of 5-hydroxymethyl furfural (HMF) and its implications on product distribution in *Saccharomyces cerevisiae*", *Applied Microbiology and Biotechnology*, 2008, vol. 78, pp. 939-945.
Alvira, P., et al., "Pretreatment technologies for an efficient bioethanol production process based on enzymatic hydrolysis: A review", *Bioresource Technology*, 2010, vol. 101, pp. 4851-4861.
Amann, E., et al., "Tightly regulated *tac* promoter vectors useful for the expression of unfused and fused proteins in *Escherichia coli*", *Gene*, 1988, vol. 69, pp. 301-315.
Carole, T.M., et al., "Opportunities in the industrial biobased products industry", *Applied Biochemistry and Biotechnology*, 2004, vol. 113-116, pp. 871-885.
Frick, O., et al., "Characterization of the metabolic shift between oxidative and fermentative growth in *Saccharomyces cerevisiae* by comparative $^{13}C$ flux analysis", *Microbial Cell Factories*, 2005, vol. 4, p. 30-46.
Geddes, C.C., et al., "Optimizing the saccharification of sugar cane bagasse using dilute phosphoric acid followed by fungal cellulases", *Bioresource Technology*, 2010, vol. 101, pp. 1851-1857.
Geddes, C.C., et al., "Simplified process for ethanol production from sugarcane bagasse using hydrolysate-resistant *Escherichia coli* strain MM160", *Bioresource Technology*, 2010, vol. 102, pp. 2702-2711.
Guo, K., et al., "Characterization of human DHRS6, an orphan short chain dehydrogenase/reductase enzyme: a novel, cytosolic type 2 R-beta-hydroxybutyrate dehydrogenase", *Journal of Biological Chemistry*, 2006, vol. 281, pp. 10291-10297.

(Continued)

*Primary Examiner* — Christian Fronda
(74) *Attorney, Agent, or Firm* — Saliwanchik, Lloyd & Eisenschenk

(57) ABSTRACT

The subject invention pertains to overexpression of a putative oxidoreductase (ucpA) for increasing furfural tolerance in genetically modified microorganisms. Genetically modified microorganisms capable of overexpressing UcpA are also provided. Increased expression of ucpA was shown to increase furfural tolerance by 50%, and to permit the fermentation of sugars to products in the presence of 15 mM furfural.

12 Claims, 7 Drawing Sheets

(56) References Cited

OTHER PUBLICATIONS

Grabowska, D., et al., "The *ALD6* gene product is indispensable for providing NADPH in yeast cells lacking glucose-6-phosphate dehydrogenase activity", *Journal of Biological Chemistry*, 2003, vol. 278, No. 16, pp. 13984-13988.

Jantama, K., et al., "Eliminating side products and increasing succinate yields in engineered strains of *Escherichia coli* C", *Biotechnology and Bioengineering*, 2008, vol. 101, No. 5, pp. 881-893.

Jarboe, L.R., et al., "Development of ethanologenic bacteria", *Advances in Biochemical Engineering/Biotechnology*, 2007, vol. 108, pp. 237-261.

Jarboe, L.R., et al., "Metabolic engineering for production of biorenewable fuels and chemicals: Contributions of synthetic biology", *Journal of Biomedicine and Biotechnology*, 2010, Article No. 761042, pp. 1-18.

Laadan, B., et al., "Identification of an NADH-dependent 5-hydroxymethylfurfural-reducing alcohol dehydrogenase in *Saccharomyces cerevisiae*", *Yeast*, 2008, vol. 25, pp. 191-198.

Liu, Z.L., "Genomic adaptation of ethanologenic yeast to biomass conversion inhibitors", *Applied Microbiology and Biotechnology*, 2006, vol. 73, pp. 27-36.

Liu, Z.L., et al., "A novel NADPH-dependent aldehyde reductase gene from *Saccharomyces cerevisiae* NRRL Y-12632 involved in the detoxification of aldehyde inhibitors derived from lignocellulosic biomass conversion", *Gene*, 2009, vol. 446, pp. 1-10.

Liu, Z.L., et al., "Multiple gene-mediated NAD(P)H-dependent aldehyde reduction is a mechanism of in situ detoxification of furfural and 5-hydroxymethylfurfural by *Saccharomyces cerevisiae*", *Applied Microbiology and Biotechnology*, 2008, vol. 81, pp. 743-753.

Martinez, A., et al., "Detoxification of dilute acid hydrolysates of lignocellulose with lime", *Biotechnology Progress*, 2001, vol. 17, pp. 287-293.

Martinez, A., et al., "Effects of Ca(OH)$_2$ treatments ("overliming") on the composition and toxicity of bagasse hemicellulose hydrolysates", *Biotechnology and Bioengineering*, 2000, vol. 69, pp. 526-536.

Martinez, A., et al., "Use of UV absorbance to monitor furans in dilute acid hydrolysates of biomass", *Biotechnology Progress*, 2000, vol. 16, pp. 637-641.

Miller, E.N., et al., "Furfural inhibits growth by limiting sulfur assimilation in ethanologenic *Escherichia coli* strain LY180", *Applied and Environmental Microbiology*, 2009, vol. 75, No. 19, pp. 6132-6141.

Miller, E.N., et al., "Genetic changes that increase 5-hydroxymethyl furfural resistance in ethanol-producing *Escherichia coli* LY180", *Biotechnology Letters*, 2010, vol. 32, pp. 661-667.

Miller, E.N., et al., "Silencing of NADPH-dependent oxidoreductase genes (*yqhD* and *dkgA*) in furfural-resistant ethanologenic *Escherichia coli*", *Applied and Environmental Microbiology*, 2009, vol. 75, No. 13, pp. 4315-4323.

Mills, T.Y., et al., "Cellulosic hydrolysate toxicity and tolerance mechanisms in *Escherichia coli*", *Biotechnology for Biofuels*, 2009, vol. 2, p. 26.

Park, S.M., et al., "Metabolic and physiological studies of *Corynebacterium glutamicum* mutants", *Biotechnology and Bioengineering*, 1997, vol. 55, pp. 864-879.

Saha, B.C., "Hemicellulose bioconversion", *Journal of Industrial Microbiology and Biotechnology*, 2003, vol. 30, pp. 279-291.

Sauer, U., et al., "The soluble and membrane-bound transhydrogenases UdhA and PntAB have divergent functions in NADPH metabolism of *Escherichia coli*", *Journal of Biological Chemistry*, 2004, vol. 279, No. 8, pp. 6613-6619.

Sirko, A., et al., "Characterization of the *Escherichia coli* gene encoding a new member of the short-chain dehydrogenase/reductase (SDR) family", *Acta Biochimica Polonica*, 1997, vol. 44, No. 1, pp. 153-157.

Turner, P.C., et al., "YqhC regulates transcription of the adjacent *Escherichia coli* genes *yqhD* and *dkgA* that are involved in furfural tolerance", *Journal of Industrial Microbiology and Biotechnology*, 2011, vol. 38, pp. 431-439.

Wang, X., et al., "Increased furfural tolerance due to overexpression of NADH-dependent oxidoreductase FucO in *Escherichia coli* strains engineered for the production of ethanol and lactate", *Applied and Environmental Microbiology*, 2011, vol. 77, No. 15, pp. 5132-5140.

Wang, X., et al., "Overexpression of NADH-dependent oxidoreductase fucO increases furfural tolerance in *Escherichia coli* strains engineered for the production of ethanol and lactate", *Applied Environmental Microbiology*, 2011, doi:10.1128/AEM.05008-11.

Zaldivar, J., et al., "Effect of alcohol compounds found in hemicellulose hydrolysate on the growth and fermentation of ethanologenic *Escherichia coli*", *Biotechnology and Bioengineering*, 2000, vol. 68, pp. 524-530.

Zaldivar, J., et al., "Effect of selected aldehydes on the growth and fermentation of ethanologenic *Escherichia coli*", *Biotechnology and Bioengineering*, 1999, vol. 65, pp. 24-33.

Zhang, X., et al., "Metabolic evolution of energy-conserving pathways for succinate production in *Escherichia coli*", *Proceedings of the National Academy of Sciences of the U.S.A.*, 2009, vol. 106, No. 48, pp. 20180-20185.

Heer, D. et al. "Resistance of *Saccharomyces cerevisiae* to High Concentrations of Furfural Is Based on NADPH-Dependent Reduction by at Least Two Oxireductases" *Applied and Environmental Microbiology*, Dec. 2009, pp. 7631-7638, vol. 75, No. 24.

Wang, X. et al. "Increased Furan Tolerance in *Escherichia coli* Due to a Cryptic *ucpA* Gene" *Applied and Environmental Microbiology*, Apr. 2012, pp. 2452-2455, vol. 78, No. 7.

Written Opinion in International Application No. PCT/US2012/045912, Jan. 3, 2013, pp. 1-6.

Runquist, D. et al. "Increased expression of the oxidative pentose phosphate pathway and gluconeogenesis in anaerobically growing xylose-utilizing *Saccharomyces cerevisiae*" *Microbial Cell Factories*, Sep. 24, 2009, pp. 1-12, vol. 8, No. 49.

Reed, J. L. et al. "An expanded genome-scale model of *Escherichia coli* K-12 (*i*JR904 GSM/GPR)" *Genome Biology*, Aug. 28, 2003, pp. R54.1-R54.12, vol. 4, No. 8, Article R54.

\* cited by examiner

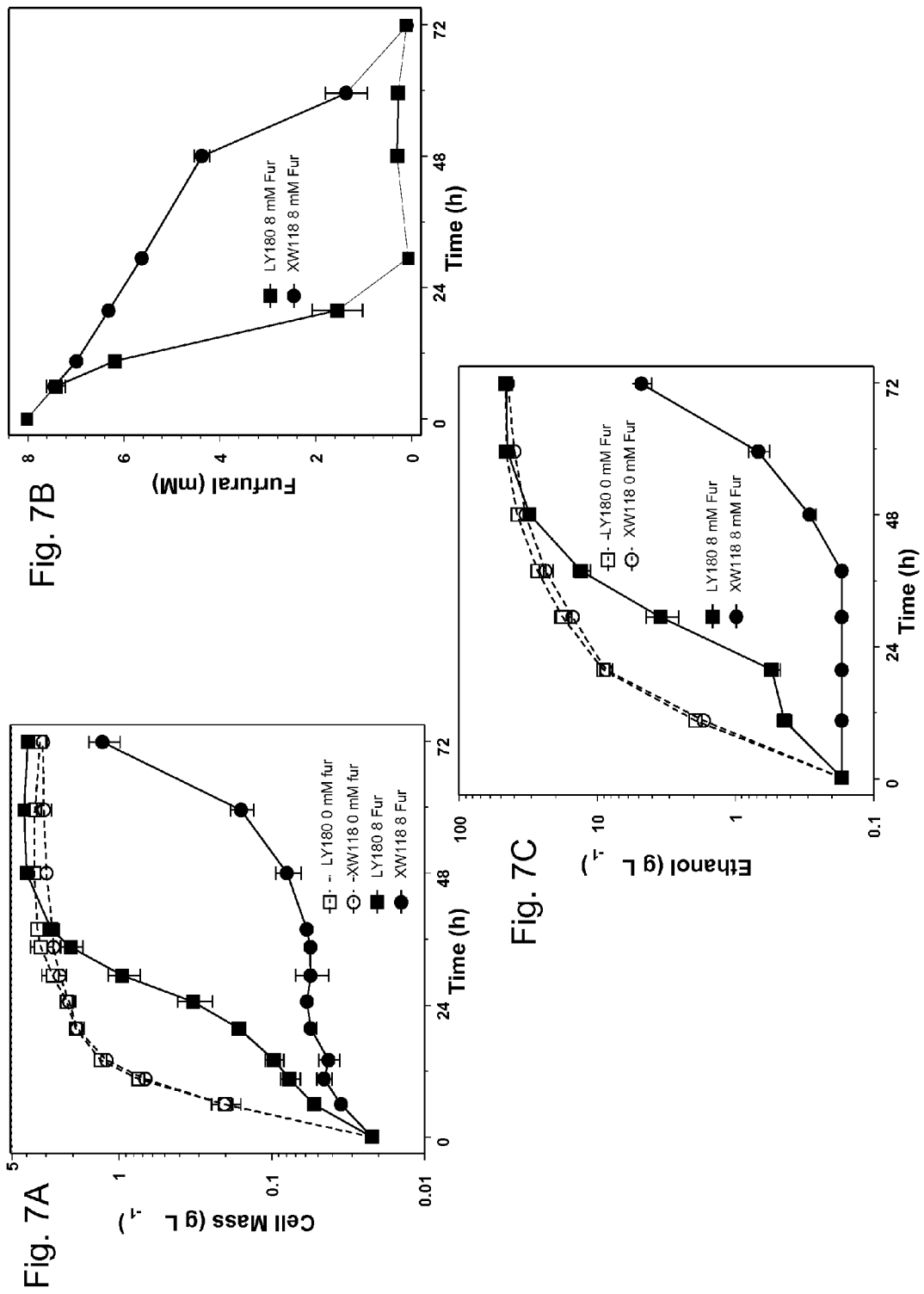

SEQUENCE LISTING

```
<160> NUMBER OF SEQ ID NOS: 10

<210> SEQ ID NO 1
<211> LENGTH: 263
<212> TYPE: PRT
<213> ORGANISM: Escherichia coli

<400> SEQUENCE: 1

Met Gly Lys Leu Thr Gly Lys Thr Ala Leu Ile Thr Gly Ala Leu Gln
1               5                   10                  15

Gly Ile Gly Glu Gly Ile Ala Arg Thr Phe Ala Arg His Gly Ala Asn
            20                  25                  30
```

| | | | | | | | | | | | | |
|---|---|---|---|---|---|---|---|---|---|---|---|---|
|Leu|Ile|Leu|Leu|Asp|Ile|Ser|Pro|Glu|Ile|Glu|Lys|Leu|Ala|Asp|Glu|
| | |35| | | |40| | | |45| | | | | |

Leu Cys Gly Arg Gly His Arg Cys Thr Ala Val Val Ala Asp Val Arg
 50                      55                      60

Asp Pro Ala Ser Val Ala Ala Ile Lys Arg Ala Lys Glu Lys Glu
65                   70                  75                  80

Gly Arg Ile Asp Ile Leu Val Asn Asn Ala Gly Val Cys Arg Leu Gly
                 85                  90                  95

Ser Phe Leu Asp Met Ser Asp Asp Arg Asp Phe His Ile Asp Ile
            100                 105                 110

Asn Ile Lys Gly Val Trp Asn Val Thr Lys Ala Val Leu Pro Glu Met
            115                 120                 125

Ile Ala Arg Lys Asp Gly Arg Ile Val Met Met Ser Ser Val Thr Gly
            130                 135                 140

Asp Met Val Ala Asp Pro Gly Glu Gln Ala Tyr Ala Leu Thr Lys Ala
145                 150                 155                 160

Ala Ile Val Gly Leu Thr Lys Ser Leu Ala Val Glu Tyr Ala Gln Ser
                165                 170                 175

Gly Ile Arg Val Asn Ala Ile Cys Pro Gly Tyr Val Arg Thr Pro Met
            180                 185                 190

Ala Glu Ser Ile Ala Arg Gln Ser Asn Pro Glu Asp Pro Glu Ser Val
            195                 200                 205

Leu Thr Glu Met Ala Lys Ala Ile Pro Met Arg Arg Leu Ala Asp Pro
            210                 215                 220

Leu Glu Val Gly Glu Leu Ala Ala Phe Leu Ala Ser Asp Glu Ser Ser
225                 230                 235                 240

Tyr Leu Thr Gly Thr Gln Asn Val Ile Asp Gly Gly Ser Thr Leu Pro
                245                 250                 255

Glu Thr Val Ser Val Gly Ile
            260

<210> SEQ ID NO 2
<211> LENGTH: 1000
<212> TYPE: DNA
<213> ORGANISM: Escherichia coli

<400> SEQUENCE: 2

```
accgatttac tgtttgttgg ccttgtgcaa ctcaatgatg tggagtcatt gaaaatgatt      60
cagcgcagca gtgagctaac acaacgcctg aaatgatgca taaagcagcg actggattga     120
gatttcctg  aattagtgag ctgatccgca gcaatatttt gtttatcctg tattttcaga     180
gggaatggag tgtaacgctc tgtattaaca aggagagcat taaaatgggt aaactcacgg     240
gcaagacagc actgattacg ggcgcattgc agggaattgg cgaaggaatt gccagaactt     300
ttgcacgtca tggcgcgaac ctaatcttgc tggatatctc ccctgagatc gaaaagctgg     360
cggacgaact gtgtggtcgt ggtcatcgct gtacggcggt tgtcgccgat gtgcgtgacc     420
cggcgtcggt agccgcagct atcaaacgcg cgaaggaaaa agaagggcgc attgatatcc     480
tggtgaataa cgcaggcgtt tgtcgtctgg gcagtttcct cgatatgagc gatgacgatc     540
gcgatttcca tattgacatc aatattaaag gcgtatggaa cgtcacgaag gcggtgctgc     600
cggagatgat tgcccgcaaa gatggtcgca ttgtgatgat gtcttcagtc actggtgata     660
tggtggccga tcctggcgaa caggcgtacg cccttacgaa agcggcgatt gttggcctga     720
caaaatcgct ggcggtggag tacgcgcagt ctggtattcg cgttaacgcc atttgcccgg     780
```

-continued

```
gatacgtgcg cacaccaatg gcggaaagca ttgcccgcca gtcgaacccg gaagatccag    840
agtcggtgct gactgaaatg gcgaaagcaa tcccgatgcg tcgcctcgcc gatccgctgg    900
aagtcggcga actggcggcc ttcctcgcat cggatgaatc cagctattta accggtacac    960
agaatgtgat tgatggcggc agcacactgc cggagacggt                         1000
```

<210> SEQ ID NO 3
<211> LENGTH: 32
<212> TYPE: DNA
<213> ORGANISM: Artificial sequence
<220> FEATURE:
<223> OTHER INFORMATION: xdhABC forward primer

<400> SEQUENCE: 3

```
gcgcgccccg ggtatggaag cgcgggaagc aa                                   32
```

<210> SEQ ID NO 4
<211> LENGTH: 32
<212> TYPE: DNA
<213> ORGANISM: Artificial sequence
<220> FEATURE:
<223> OTHER INFORMATION: xdhABC reverse primer

<400> SEQUENCE: 4

```
gcgcgcggat cccggcattg ctacgctcta tc                                   32
```

<210> SEQ ID NO 5
<211> LENGTH: 32
<212> TYPE: DNA
<213> ORGANISM: Artificial sequence
<220> FEATURE:
<223> OTHER INFORMATION: aldA forward primer

<400> SEQUENCE: 5

```
cgcgcggaat tcataaatca caggagtcgc cc                                   32
```

<210> SEQ ID NO 6
<211> LENGTH: 32
<212> TYPE: DNA
<213> ORGANISM: Artificial sequence
<220> FEATURE:
<223> OTHER INFORMATION: aldA revverse primer

<400> SEQUENCE: 6

```
cgcgcgaagc tttcgcctgg tacgataacg aa                                   32
```

<210> SEQ ID NO 7
<211> LENGTH: 40
<212> TYPE: DNA
<213> ORGANISM: Artificial sequence
<220> FEATURE:
<223> OTHER INFORMATION: yeiTA forward primer

<400> SEQUENCE: 7

```
ggaattcctt aattactcat agcattaagg aagatcacat                           40
```

<210> SEQ ID NO 8
<211> LENGTH: 38
<212> TYPE: DNA
<213> ORGANISM: Artificial sequence
<220> FEATURE:
<223> OTHER INFORMATION: yeiTA reverse primer

<400> SEQUENCE: 8

```
gcgaagcttg taattatttt taccgtcatc aactatgg                             38
```

```
<210> SEQ ID NO 9
<211> LENGTH: 27
<212> TYPE: DNA
<213> ORGANISM: Artificial sequence
<220> FEATURE:
<223> OTHER INFORMATION: ucpA forward primer

<400> SEQUENCE: 9
ggaattcacg ctctgtatta acaagga                                        27

<210> SEQ ID NO 10
<211> LENGTH: 30
<212> TYPE: DNA
<213> ORGANISM: Artificial sequence
<220> FEATURE:
<223> OTHER INFORMATION: ucpA reverse primer

<400> SEQUENCE: 10
agccaagctt cggacgtgaa aggagtaacg                                     30
```

US 9,347,077 B2

OVER-EXPRESSION OF A PUTATIVE OXIDOREDUCTASE (UCPA) FOR INCREASING FURFURAL OR 5-HYDROXYMETHYLFURFURAL TOLERANCE

CROSS-REFERENCE TO RELATED APPLICATION APPLICATIONS

This application is the U.S. national stage application of International Patent Application No. PCT/US2012/045912, filed Jul. 9, 2012, which claims the benefit of U.S. Provisional Application Ser. No. 61/505,684, filed Jul. 8, 2011, the disclosures of which are hereby incorporated by reference in their entirety, including all figures, tables and amino acid or nucleic acid sequences.

This invention was made with government support under DE-FG36-08GO88142 awarded by Department of Energy and under 2001-10006-30358 awarded by the Department of Agriculture. The government has certain rights in the invention.

The Sequence Listing for this application is labeled "SeqList-replace.txt" which was created on Feb. 1, 2014 and is 6 KB. The entire contents of the sequence listing is incorporated herein by reference in its entirety.

BACKGROUND OF THE INVENTION

Carbohydrate components of woody biomass (cellulose and hemicellulose) represent an abundant potential source of sugars for microbial conversion into renewable fuels, plastics, and other chemicals (Carole et al., 2004; Jarboe et al., 2007; Jarboe et al., 2010; Saha et al., 2003). However, cost-effective depolymerization of this complex material to produce fermentable sugar streams remains a major challenge (Alvira et al., 2010; Saha et al., 2003). Pretreatment processes such as diluting mineral acids at elevated temperature and pressures open the structure of woody biomass to increase the effectiveness of cellulase enzymes, and hydrolyze the pentose polymers of hemicellulose into monomers. Unwanted side reactions from this pretreatment also produce a mixture of compounds (furans, acetate, soluble products from lignin, and others) that inhibit growth and retard fermentation (Almeida et al., 2009; Jarboe et al., 2007; Mills et al., 2009). Most inhibitors can be removed or neutralized by separating the solubilized sugars from the cellulose-enriched fiber using counter-current washing followed by over-liming (Martinez et al., 2001; Martinez et al., 2000a). However, these added process steps would also add cost to renewable products. By developing robust biocatalysts that are resistant to side products from pretreatment it should be possible to design a simpler process (Geddes et al., 2010a, b).

Furfural, the dehydration product of xylose, is of particular importance as a fermentation inhibitor in hemicellulose hydrolysates (Almeida et al., 2009; Mills et al., 2009). Furfural concentrations in hemicellulose hydrolysates have been correlated with toxicity (Zaldivar et al., 1999). The addition of furfural to over-limed hemicellulose hydrolysates has been shown to restore toxicity (Martinez et al., 2001; Martinez et al., 2000a). In model studies with various hydrolysate inhibitors, furfural was unique in potentiating the toxicity of other compounds (Zaldivar et al., 1999). Furan alcohols (reduced products) are less toxic than the respective aldehydes (Zaldivar et al., 2000; Zaldivar et al., 1999). Furfural-resistant mutants of ethanologenic *Escherichia coli* have been isolated and characterized (Miller et al., 2009a, b; Turner et al., 2010).

Resistance to low concentrations of furfural was found to result from the silencing of yqhD, an NADPH-dependent, furfural oxidoreductase that is induced by furfural (Miller et al., 2009a, b; Turner et al., 2010). Although there are multiple NADPH-furfural reductases in *E. coli* and conversion of furfural to the less toxic alcohol which would be generally regarded as beneficial, the unusually low $K_m$ of YqhD for NADPH appears to create a metabolic conflict by competing with biosynthesis for NADPH (Miller et al., 2009a). Metabolic routes for the anaerobic production of NADPH during xylose fermentation are quite limited (Frick et al., 2005; Grabowska et al., 2003; Milles et al., 2009). The metabolism of furfural by YqhD is proposed to inhibit growth and fermentation by depleting the pool of NADPH below that required for essential biosynthetic reactions (Miller et al., 2009a, b; Turner et al., 2010). Sulfate assimilation was identified as a site that is particularly sensitive to NADPH limitation (Miller et al., 2009a). Furan toxicity (furfural and 5-HMF) can be minimized by a variety of approaches that increase the availability of NADPH (Miller et al., 2009a, b; Miller et al., 2010). The pntAB-encoded, membrane transhydrogenase has also been shown to increase furfural tolerance by directly supplying NADPH using NADH as the electron donor (Miller et al., 2009a, b; Miller et al., 2010).

Low levels of NADH-dependent oxidoreductases appear to be present in crude extracts of *E. coli*. Furfural reduction by these should not affect the NADPH and would eliminate competition during biosynthesis. One gene, fucO, has been previously discovered to be an NADH-dependent oxidoreductase that reduces furfural and hydroxymethyl furfural. Increased expression of fucO was shown to increase cell tolerance to furfural (Wang et al., 2011a).

Further studies were undertaken to identify additional NAD(P)H-oxidoreductases that could reduce furfural and confer increased furfural tolerance using expression arrays that examine the entire genome. These were not successful. Instead, we made the unexpected discovery of a novel gene (ucpA) that confers furfural tolerance by an unknown mechanism, although UcpA has a putative NAD(P)H-binding site and shares some similarity with some short chain oxidoreductases (Sirko et al., 1997) that allowed identification as a candidate gene. There is very little published literature about UcpA. UcpA does not encode furfural reductase activity based on in vitro assays and whole cell (in vivo) assays. UcpA also does not exhibit transhydrogenase activity. The mechanism of UcpA action that leads to increased furfural tolerance remains unknown.

Reduction of educe furfural with NADH or increased production of NADPH have been shown to be effective approaches to increase furfural tolerance (Miller et al., 2009a, b; Miller et al., 2010; Wang et al., 2011a) and a need for providing various means for increasing furfural resistance in genetically modified microorganisms remains.

BRIEF SUMMARY OF THE INVENTION

Furfural is an important fermentation inhibitor in hemicellulose sugar syrups derived from woody biomass that are to be fermented by various microorganisms and there remains a need for providing various means by which furfural-mediated inhibition of hemicellulose fermentation can be overcome. Overexpression of ucpA confers furfural tolerance and 5-hydroxymethylfurfural (5-HMF) in genetically modified microorganisms. Accordingly, various aspects of the invention provide materials and methods for the fermentation of hemicellulose sugar syrups that contain furfural, particularly using bacterial, fungal and yeast cells for the production of desired products. Thus, novel biocatalysts (bacterial, fungal and yeast cells) exhibiting increased tolerance to furfural and 5-hydroxymethylfurfural (5-HMF) are provided, as are methods of making and using such biocatalysts.

BRIEF DESCRIPTION OF THE DRAWINGS

FIG. 2A. NADH-dependent reduction of furfural (A) or 5-HMF (B) by cell-free extracts of LY180 containing vector alone (pTrc99A) or IPTG-induced ucpA, yeiTA, aldA, xdhABC. FIG. 2C. NADPH-dependent reduction of furfural or 5-HMF by cell-free extracts of LY180 containing vector alone (pTrc99A) or IPTG-induced ucpA in LY180. FIG. 2D. In vivo furfural (10 mM) reduction by chloramphenicol-inhibited, non-growing cells (LY180, 0.88 mg cell dry weight ml$^{-1}$) containing vector alone (pTrc99A) or 0.1 mM IPTG-induced ucpA in LY180(pLOI4856).

FIG. 3A. LY180(pLOI4856) and furfural; FIG. 3B. LY180(pLOI4856) and 5-HMF; FIG. 3C. KJ122 (pLOI4856) and furfural; FIG. 3D. KJ122(pLOI4856) and 5-HMF. An uninduced vector (pTrc99A) control was included as a reference.

FIG. 5A. SDS-Page gel electrophoresis comparing proteins from strain LY180(pLOI4856) expressing ucpA to a control strain harboring vector alone (pTrc99A). A new band in LY180 (pLOI4856) labeled with an arrow corresponds to the predicted size of UcpA. Molecular weight markers are included on the left. FIG. 5B. (cell mass), FIG. 5C. (furfural), and FIG. 5D. (ethanol). Batch fermentations in pH-controlled fermentation vessels in the absence and presence of furfural (15 mM). Expression of ucpA from pLOI4856 (0.1 mM IPTG) was compared to the vector control, LY180(pTrc99A). Controls were included without furfural (open symbols and dotted lines). Under these conditions, LY180 (Trc99A) was unable to grow but continued to metabolize furfural.

FIG. 6A. Effect of ucpA plasmid (pLOI4856) on MIC for furfural. FIG. 6B. Effect of pLOI4856 on growth in 10 mM furfural. FIG. 6C. Effect of pLOI4856 on ethanol production in 10 mM furfural. FIG. 6D. Effect of pLOI4856 on furfural metabolism during fermentation. Controls were included without furfural (dotted lines).

FIGS. 7A-7C. Deletion of chromosomal ucpA (XW118) decreased furfural tolerance of LY180 during pH-controlled fermentations (10% xylose). FIG. 7A. Cell mass; FIG. 7B. Furfural metabolism; FIG. 7C. Ethanol. Controls were included without furfural (dotted lines).

DETAILED DISCLOSURE OF THE INVENTION

Figure 1A:
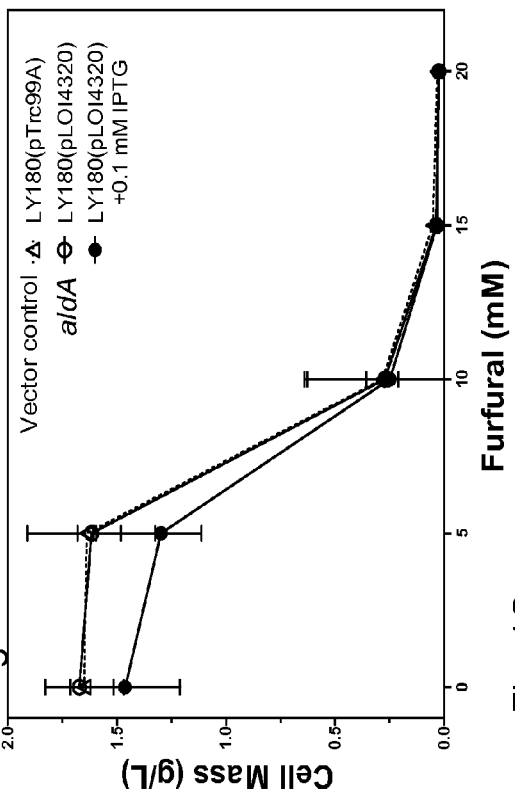
FIG. 1. Effect of aldA, ucpA, xdhABC, yeiTA overexpression in LY180 growth in the presence of furfural. Growth inhibition of LY180 with vector alone (pTrc99A) (Δ, 0 mM IPTG) or plasmids encoding (A) aldA, (B) ucpA, (C) xdhABC or (D) yeiTA (○, 0 mM IPTG; ●, plasmid induced with 0.1 mM IPTG) by furfural at indicated concentrations.

The invention provides organisms for production of renewable fuels and other chemicals. Particularly, the invention provides bacteria, fungi and yeasts that can grow and produce renewable fuels and other chemicals in the presence of increased furfural. The invention provides for an isolated or recombinant cell/microorganism (bacterial, yeast or fungal cell) having increased expression of ucpA and exhibiting improved ability to produce a desired product in the presence of furfural and 5-HMF as compared to a reference cell (e.g., a reference bacterial, yeast or fungal cell). In various embodiments, the bacterial, fungal or yeast cell has increased furfural and 5-HMF tolerance as compared to a reference bacterial, fungal or yeast cell. The bacterial, fungal or yeast cell having increased furfural tolerance may be a wild-type bacterial, fungal or yeast cell that was selected for increased furfural and/or 5-HMF tolerance that is conferred by increased expression or activity of UcpA. In various embodiments, the bacterial, fungal or yeast cell having increased furfural and/or 5-HMF tolerance can produce ethanol; lactic acid; succinic acid; malic acid; acetic acid; 1,3-propanediol; 2,3-propanediol; pyruvate; dicarboxylic acids; adipic acid; butanol; and amino acids, including aliphatic and aromatic amino acids.

Various publications have disclosed bacterial, fungal or yeast cells in which ethanol; lactic acid; succinic acid; malic acid; acetic acid; 1,3-propanediol; 2,3-propanediol; 1,4-butanediol; 2,3-butanediol; butanol; pyruvate; dicarboxylic acids; adipic acid; and amino acids, including aliphatic and aromatic amino acids, can be produced. Many of these microorganisms have been genetically manipulated (genetically engineered) in order to produce these desired products. Exemplary publications in this regard include U.S. Published Patent Applications US-2010/0184171A1 (directed to the production of malic acid and succinic acid), 2009/0148914A1 (directed to the production of acetic acid; 1,3-propanediol; 2,3-propanediol; pyruvate; dicarboxylic acids; adipic acid; and amino acids, including aliphatic and aromatic amino acids), 2007/0037265A1 (directed to the production of chirally pure D and L lactic acid) and PCT application PCT/US2010/029728 (published as WO2010/115067 and directed to the production of succinic acid). The teachings of each of these publications, with respect to the production of bacterial cells producing a desired product, are hereby incorporated by reference in their entirety.

In another aspect of the invention, bacterial, fungal or yeast cells disclosed herein demonstrate increased growth in the presence of furfural and/or 5-HMF as compared to reference bacterial, fungal or yeast cells. In another embodiment, the bacterial, fungal or yeast cells have increased growth in the presence of furfural and/or 5-HMF at concentrations of about 5 mM, 10 mM, 15 mM, 20 mM, 25 mM, 30 mM, 35 mM, 40 mM or higher (or between about 5 mM and about 20 mM furfural and/or 5-HMF, about 15 mM to about 30 mM furfural and/or 5-HMF, preferably about 15 mM furfural and/or 5 HMF).

Yet other aspects of the invention provide bacterial cells, fungal cells and yeast cells that demonstrate increased furfural and/or 5-HMF tolerance and have increased UcpA activity, as compared to reference bacterial, fungal or yeast cells. Bacterial cells can be selected from Gram negative bacteria or Gram positive bacteria. In this aspect of the invention, the Gram-negative bacterial cell can be selected from the group consisting of *Escherichia, Zymomonas, Acinetobacter, Gluconobacter, Geobacter, Shewanella, Salmonella, Enterobacter* and *Klebsiella*. Gram-positive bacteria can be selected from the group consisting of *Bacillus, Clostridium, Corynebacterial, Lactobacillus, Lactococcus, Oenococcus, Streptococcus* and *Eubacterial* cells. Various thermophilic bacterial cells, such as *Thermoanaerobes* (e.g., *Thermoanaerobacterium saccharolyticum*) can also be manipulated to increase furfural resistance and/or 5-HMF resistance via increased expression of UcpA. Other thermophilic microorganisms include, but are not limited to, *Bacillus* spp., e.g., *Bacillus coagulans* strains, *Bacillus licheniformis* strains, *Bacillus subtilis* strains, *Bacillus amyloliquifaciens* strains, *Bacillus megaterium* strains, *Bacillus macerans* strains, *Paenibacillus* spp. strains or *Geobacillus* spp. such as *Geobacillus stearothermophilus* strains can be genetically modified. Other *Bacillus* strains can be obtained from culture collections such as ATCC (American Type Culture Collection) and modified to have increased UcpA activity.

Other embodiments provide for a yeast cell or fungal cell having increased UcpA activity. The yeast cell may be a *Candida, Hansenula, Kluyveromyces, Pichia, Saccharomyces, Schizosaccharomyces*, or *Yarrowia* cell such as a *Kluyveromyces lactis, Saccharomyces carlsbergensis, Saccharomyces cerevisiae, Saccharomyces diastaticus, Saccharomyces douglasii, Saccharomyces kluyveri, Saccharomyces norbensis, Saccharomyces oviformis*, or *Yarrowia lipolytica* cell.

In other embodiments, the cell having increased UcpA activity may be a fungal cell. "Fungi" as used herein includes the phyla Ascomycota, Basidiomycota, Chytridiomycota, Zygomycota, and Oomycota and all mitosporic fungi. A fungal cell may be a yeast cell. "Yeast" as used herein includes ascosporogenous yeast (Endomycetales), basidiosporogenous yeast, and yeast belonging to the Fungi Imperfecti (Blastomycetes). Since the classification of yeast may change in the future, for the purposes of this invention, yeast shall be defined as described in Biology and Activities of Yeast (Skinner, F. A., Passmore, S. M., and Davenport, R. R., eds, Soc. App. Bacteriol. Symposium Series No. 9, 1980).

The fungal host cell may be a filamentous fungal cell. "Filamentous fungi" include all filamentous forms of the subdivision Eumycota and Oomycota (as defined by Hawksworth et al., Ainsworth and Bisby's Dictionary of The Fungi, 8th edition, 1995, CAB International, University Press, Cambridge, UK). The filamentous fungi are generally characterized by a mycelial wall composed of chitin, cellulose, glucan, chitosan, mannan, and other complex polysaccharides. Vegetative growth is by hyphal elongation and carbon catabolism is obligately aerobic. In contrast, vegetative growth by yeasts such as *Saccharomyces cerevisiae* is by budding of a unicellular thallus and carbon catabolism may be fermentative.

The filamentous fungal host cell may be an *Acremonium, Aspergillus, Aureobasidium, Bjerkandera, Ceriporiopsis, Chrysosporium, Coprinus, Coriolus, Cryptococcus, Filibasidium, Fusarium, Humicola, Magnaporthe, Mucor, Myceliophthora, Neocallimastix, Neurospora, Paecilomyces, Penicillium, Phanerochaete, Phlebia, Piromyces, Pleurotus, Schizophyllum, Talaromyces, Thermoascus, Thielavia, Tolypocladium, Trametes*, or *Trichoderma* cell. For example, the filamentous fungal host cell may be an *Aspergillus awamori, Aspergillus foetidus, Aspergillus fumigatus, Aspergillus japonicus, Aspergillus nidulans, Aspergillus niger, Aspergillus oryzae, Bjerkandera adusta, Ceriporiopsis aneirina, Ceriporiopsis caregiea, Ceriporiopsis gilvescens, Ceriporiopsis pannocinta, Ceriporiopsis rivulosa, Ceriporiopsis subrufa, Ceriporiopsis subvermispora, Chrysosporium inops, Chrysosporium keratinophilum, Chrysosporium lucknowense, Chrysosporium merdarium, Chrysosporium pannicola, Chrysosporium queenslandicum, Chrysosporium tropicum, Chrysosporium zonatum, Coprinus cinereus, Coriolus hirsutus, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides, Fusarium venenatum, Humicola insolens, Humicola lanuginosa, Mucor miehei, Myceliophthora thermophile, Neurospora crassa, Penicillium purpurogenum, Phanerochaete chrysosporium, Phlebia radiata, Pleurotus eryngii, Thielavia terrestris, Trametes villosa, Trametes versicolor, Trichoderma harzianum, Trichoderma koningii, Trichoderma longibrachiatum, Trichoderma reesei*, or *Trichoderma viride* cell.

Fungal cells may be transformed by a process involving protoplast formation, transformation of the protoplasts, and regeneration of the cell wall in a manner known per se. Suitable procedures for transformation of *Aspergillus* and *Trichoderma* host cells are described in EP 238023, Yelton et al., 1984, Proc. Natl. Acad. Sci. USA 81: 1470-1474, and Christensen et al., 1988, Bio/Technology 6: 1419-1422. Suitable methods for transforming *Fusarium* species are described by Malardier et al., 1989, Gene 78: 147-156, and WO 96/00787. Yeast may be transformed using the procedures described by Becker and Guarente, In Abelson, J. N. and Simon, M. I., editors, Guide to Yeast Genetics and Molecular Biology, Methods in Enzymology, Volume 194, pp 182-187, Academic Press, Inc., New York; Ito et al., 1983, J. Bacteriol. 153: 163; and Hinnen et al., 1978, Proc. Natl. Acad. Sci. USA 75: 1920.

In various embodiments within this aspect of the invention, the bacterial cells can be *Escherichia coli* or *Klebsiella oxytoca* that have, optionally, been genetically modified to produce a desired product. In these embodiments, an isolated or recombinant bacterial cell is provided wherein UcpA activity is increased as compared to a reference bacterial cell. In certain embodiments of this aspect of the invention, bacterial cells can also have increased FucO activity, as described in U.S. Provisional Patent Application 61/470,642, filed Apr. 1, 2011 (the disclosure of which is hereby incorporated in its entirety).

The activity of UcpA can be increased in a variety of ways. For example, UcpA activity can be increased by expression of the ucpA gene in a multicopy plasmid with a native promoter or any other promoter sequence which is known to increase gene expression. Expression of UcpA can also be increased by integrating additional copies of the ucpA gene within the chromosome of a bacterial cell using transposons. Alternatively, the native promoter of the ucpA gene can be replaced by other promoter elements known to enhance the level of gene expression in a bacterial cell. Similar techniques can be used for fungal and yeast cells.

Various other aspects of the invention provide methods of producing ethanol, lactic acid, succinic acid, malic acid, acetic acid, 1,3-propanediol, 2,3-propanediol, 1,4-butanediol, 2,3-butanediol, butanol, pyruvate, dicarboxylic acids, adipic acid or amino acids. In these aspects of the invention, known bacterial, fungal or yeast cells that produce ethanol, lactic acid, succinic acid, malic acid, acetic acid, 1,3-propanediol, 2,3-propanediol, 1,4-butanediol, 2,3-butanediol, pyruvate, dicarboxylic acids, adipic acid or amino acids are manipulated in a manner that results in an increase in UcpA activity for the bacterial, fungal or yeast cell (as compared to a reference bacterial, fungal or yeast cell). In various embodiments, the methods comprise culturing a bacterial, fungal or yeast cell producing a desired product (e.g., ethanol, lactic acid, succinic acid, malic acid, acetic acid, 1,3-propanediol, 2,3-propanediol, 1,4-butanediol, 2,3-butanediol, pyruvate, dicarboxylic acids, adipic acid or amino acids) and having increased UcpA activity, as compared to a reference cell, under conditions that allow for the production of the desired product. The desired product (e.g., ethanol, lactic acid, succinic acid, malic acid, acetic acid, 1,3-propanediol, 2,3-propanediol, 1,4-butanediol, 2,3-butanediol, pyruvate, dicarboxylic acids, adipic acid or amino acids) can, optionally, be purified from the culture medium in which the bacterial, fungal or yeast cell was cultured. In various other embodiments, the bacterial, fungal or yeast cell can be cultured in the presence of a hemicellulose hydrolysate.

As used herein, "isolated" refers to bacterial, fungal or yeast cells partially or completely free from contamination by other bacteria. An isolated bacterial, fungal or yeast cell (bacterial, fungal or yeast cell) can exist in the presence of a small fraction of other bacteria which do not interfere with the properties and function of the isolated bacterial, fungal or yeast cell (e.g., a bacterial, fungal or yeast cell having increased ucpA activity). An isolated bacterial, fungal or yeast cell will generally be at least 30%, 40%, 50%, 60%, 70%, 80%, 85%, 90%, 95%, 98%, or 99% pure. Preferably, an isolated bacterial, fungal or yeast cell according to the invention will be at least 98% or at least 99% pure.

A bacterial, fungal or yeast cell may be a recombinant, non-recombinant or mutant isolated from nature, provided that the bacterial, fungal or yeast cell exhibits higher levels of UcpA activity as compared to a reference strain. A non-recombinant bacterial, fungal or yeast cell includes a bacterial, fungal or yeast cell that does not contain heterologous polynucleotide sequences, and is suitable for further modification as disclosed herein, including genetic manipulation for the introduction of heterologous polynucleotide sequences. The term is intended to include progeny of the cell originally transfected. A "recombinant cell" is a bacterial, fungal or yeast cell that contains a heterologous polynucleotide sequence, or that has been treated such that a native polynucleotide sequence has been mutated or deleted. A "mutant" bacterial, fungal or yeast cell is a cell that is not identical to a reference bacterial, fungal or yeast cell, as defined herein below.

A wild-type bacterial, fungal or yeast cell is the typical form of an organism or strain, for example a bacterial cell, as it occurs in nature, in the absence of mutations. Wild-type refers to the most common phenotype in the natural population. "Parental bacterial, fungal or yeast strain", "parental bacterial strain", "parental fungal strain" or "parental yeast strain" is the standard of reference for the genotype and phenotype of a given bacterial, fungal or yeast cell and may be referred to as a "reference strain" or "reference bacterial, fungal or yeast cell". A "parental bacterial, fungal or yeast strain" may have been genetically manipulated or be a "wild-type" bacterial cell depending on the context in which the term is used. Where ucpA expression is increased in non-genetically modified bacterial, fungal or yeast cells, the reference strain or reference bacterial, fungal or yeast cell will be a wild-type bacterial, fungal or yeast cell from which the bacterial, fungal or yeast cell having increased UcpA activity was obtained as disclosed below.

The terms "increasing", "increase", "increased" or "increases" refers to increasing by at least 5%, for example, 5, 6, 7, 8, 9, 10, 15, 20, 25, 30, 35, 40, 45, 50, 55, 60, 65, 70, 75, 80, 85, 90, 95, 99, 100% or more, a particular activity (e.g., increased UcpA activity). The terms "decreasing", "decrease", "decreased" or "decreases" refers to reducing by at least 5%, for example, 5, 6, 7, 8, 9, 10, 15, 20, 25, 30, 35, 40, 45, 50, 55, 60, 65, 70, 75, 80, 85, 90, 95, 99, 100% or more, a particular activity (e.g., any decreased activity). An increase (or decrease) in activity includes an increase (or decrease) in the rate and/or the level of a particular activity (e.g., UcpA activity) or the expression of mRNA (such as mRNA encoding UcpA). "Growth" means an increase, as defined herein, in the number or mass of a bacterial, fungal or yeast cell over time.

As used herein, "UcpA activity" means an increase in the tolerance of a bacterial, fungal or yeast cell to furfural and/or 5-HMF. The nucleic and amino acid sequence of the ucpA gene (SEQ ID NO: 2) and polypeptide (UcpA; SEQ ID NO: 1) are known in the art (see, for example, EMBL-Bank Accession No. X99908.1, which is hereby incorporated in its entirety and is provided in the sequence listing appended hereto).

In one aspect of the invention, bacterial cells having increased UcpA activity can also have the activity of FucO, YqhD, YqhC and/or DkgA protein decreased or altered, as compared to the activity of YqhD, YqhC and/or DkgA protein in a reference bacterial cell or a reference bacterial cell having increased FucO activity. Activity is decreased or altered by methods known in the art, including but not limited to modification of the yqhD, yqhC and/or dkgA gene(s) (e.g. by inserting, substituting or removing nucleic acids or amino acids in the sequences encoding the genes). Thus, this aspect of the invention can also provide a bacterial cell wherein expression of ucpA and/or fucO is increased, as compared to a reference bacterial cell and expression of the yqhD, yqhC and/or dkgA gene is/are decreased as compared to the expression of the yqhD, yqhC and/or dkgA gene in a reference bacterial cell. Expression can be decreased or altered by methods known in the art, including but not limited to modification of the yqhD, yqhC and/or dkgA gene(s) (e.g. by inserting, substituting or removing nucleic acids or amino acids in the sequences encoding the genes), inactivation or knockout of these genes. Methods for altering the activity of YqhD, YqhC and/or DkgA and inactivating the genes encoding these proteins are known in the art; see for example PCT/US2010/020051 (PCT publication WO 2010101665 A1), which is hereby incorporated by reference in its entirety.

The invention provides for a bacterial, fungal or yeast cell that has an increased resistance to furfural, increased expression of UcpA protein or mRNA as compared to a reference bacterial, fungal or yeast cell, and further exhibits at least one of: 1) increased growth in the presence or absence of furfural as compared to a reference bacterial, fungal or yeast cell; 2) increased growth and increased production of a desired product as compared to a reference bacterial, fungal or yeast cell; 3) increased growth and increased production of a desired product in the presence of furfural as compared to a reference bacterial, fungal or yeast cell; 4) increased growth in the presence of a hydrolysate as compared to a reference bacterial, fungal or yeast cell; and 5) increased production of a desired product as compared to a reference bacterial, fungal or yeast cell.

The invention also provides for a bacterial, fungal or yeast cell that has an increased resistance to 5-HMF, increased expression of UcpA protein or mRNA as compared to a reference bacterial, fungal or yeast cell, and further exhibits at least one of: 1) increased growth in the presence or absence of 5-HMF as compared to a reference bacterial, fungal or yeast cell; 2) increased growth and increased production of a desired product as compared to a reference bacterial, fungal or yeast cell; 3) increased growth and increased production of a desired product in the presence of 5-HMF as compared to a reference bacterial, fungal or yeast cell; 4) increased growth in the presence of a hydrolysate as compared to a reference bacterial, fungal or yeast cell; and 5) increased production of a desired product as compared to a reference bacterial, fungal or yeast cell. Methods of increasing the resistance of a bacterial, fungal or yeast cell to furfural and 5-HMF are also provided herein.

Various aspects of the invention provide for the use of a variety of hydrolysates for the production of a desired product, including, but not limited to, hydrolysate derived from a biomass, a hemicellulosic biomass, a lignocellulosic biomass or a cellulosic biomass. Yet other aspects of the invention provide a bacterial, fungal or yeast cell with increased resistance to furfural, wherein the bacterial, fungal or yeast cell is capable of producing a desired product as a primary fermentation product, wherein optionally, the primary fermentation product is produced under anaerobic or microaerobic conditions.

As noted above, various aspects of the invention provide for an isolated or recombinant bacterial, fungal or yeast cell, wherein expression of ucpA is increased as compared to a reference bacterial, fungal or yeast cell, and wherein the bacterial, fungal or yeast cell has increased furfural tolerance as compared to the reference bacterial, fungal or yeast cell. The invention also provides for an isolated or recombinant bacterial, fungal or yeast cell wherein the expression of ucpA is increased as compared to a reference bacterial, fungal or yeast cell, furfural tolerance is increased in the isolated or recombinant bacterial, fungal or yeast cell as compared to the reference bacterial, fungal or yeast cell, and wherein the bacterial, fungal or yeast cell is capable of producing a desired product. In this aspect of the invention, the bacterial, fungal or yeast cell can be prepared recombinantly such that UcpA activity is increased or by a process comprising the steps of: (a) growing a candidate strain of the bacterial, fungal or yeast cell in the presence of furfural; and (b) selecting a bacterial, fungal or yeast cell that produces a desired product in the presence of furfural and has higher UcpA activity as compared to a reference bacterial, fungal or yeast cell or parental bacterial, fungal or yeast cell.

The invention also provides for a method for producing a desired product from a biomass, a hemicellulosic biomass, a lignocellulosic biomass, a cellulosic biomass or an oligosaccharide source comprising contacting the biomass, hemicellulosic biomass, lignocellulosic biomass, cellulosic biomass or oligosaccharide with any of the isolated or recombinant bacterial, fungal or yeast cells of the invention, thereby producing the desired product from a biomass, hemicellulosic biomass, lignocellulosic biomass, cellulosic biomass or an oligosaccharide source.

Further, the invention provides for a method for producing a desired product from a biomass, a hemicellulosic biomass, a lignocellulosic biomass, a cellulosic biomass or an oligosaccharide source in the presence of furfural comprising contacting the biomass, hemicellulosic biomass, lignocellulosic biomass, cellulosic biomass or oligosaccharide with the isolated or recombinant bacterial, fungal or yeast cell of the invention, thereby producing the desired product from a biomass, hemicellulosic biomass, lignocellulosic biomass, cellulosic biomass or an oligosaccharide source.

The subject application also provides the following non-limiting embodiments:

1. An isolated bacterial, fungal or yeast cell having increased UcpA activity as compared to a reference bacterial, fungal or yeast cell, wherein said bacterial, fungal or yeast cell having increased UcpA activity exhibits increased tolerance to furfural and/or 5-hydroxymethylfurfural (5-HMF).

2. The isolated bacterial, fungal or yeast cell of embodiment 1, wherein said bacterial, fungal or yeast cell produces a desired product or has been genetically engineered to produce a desired product selected from the group consisting of ethanol, lactic acid, succinic acid, malic acid, acetic acid, 1,3-propanediol, 2,3-propanediol, 1,4-butanediol, 2,3-butanediol, butanol, pyruvate, dicarboxylic acids, adipic acid and amino acids.

3. The isolated bacterial, fungal or yeast cell of embodiments 1-2, wherein said bacterial, fungal or yeast cell exhibits increased production of said desired product as compared to a reference bacterial, fungal or yeast cell in the presence of furfural and/or 5-hydroxymethylfurfural (5-HMF).

4. The isolated bacterial cell of embodiments 1-3, wherein:
a) expression of the yqhD gene is reduced in said bacterial cell as compared to a reference bacterial cell;
b) expression of the dkgA gene is reduced in said bacterial cell as compared to a reference bacterial cell;
c) expression of the yqhD gene, yqhC gene and/or the dkgA gene are reduced in said bacterial cell as compared to expression in a reference bacterial cell;
d) expression of the yqhC gene is reduced in said bacterial cell as compared to expression in a reference bacterial cell;
e) expression of the yqhD gene, the yqhC gene and the dkgA gene is reduced in said bacterial cell as compared to expression in a reference bacterial cell;
f) the yqhD gene is not expressed or is deleted in said bacterial cell;
g) the yqhD gene and the dkgA gene are not expressed or are deleted in said bacterial cell;
h) the yqhC gene or yqhD gene, the yqhC gene and the dkgA gene are not expressed or are deleted in said bacterial cell;
i) the yqhC gene is not expressed or is deleted in said bacterial cell;
j) the dkgA gene is not expressed in said bacterial cell;
k) the activity of the yqhD gene, yqhC gene and/or the dkgA gene product(s) are reduced in said bacterial cell as compared to expression in a reference bacterial cell; or
l) the activity of the yqhC gene product is reduced in said bacterial cell as compared to expression in a reference bacterial cell.

5. The isolated bacterial cell of embodiment 4, wherein the activity of YqhD protein is reduced in said bacterial cell as compared to a reference bacterial cell.

6. The isolated bacterial cell of embodiment 4, wherein the activity of the YqhD protein and the activity of the DkgA protein are reduced in said bacterial cell as compared to a reference bacterial cell.

7. The isolated bacterial cell of embodiment 4, wherein the activity of the YqhC protein is reduced in said bacterial cell as compared to a reference bacterial cell.

8. The isolated bacterial cell of embodiment 4, wherein regulation of the expression of the yqhD gene is altered to reduce yqhD expression as compared to a reference bacterial cell.

9. The isolated bacterial cell of embodiment 4, wherein regulation of the expression of the yqhD gene and regulation of the expression of the dkgA gene are altered to reduce yqhD and dkgA expression in said bacterial cell as compared to expression in a reference bacterial cell.

10. The isolated bacterial cell of embodiment 4, wherein regulation of expression of the yqhC gene is altered to reduce yqhC expression in said bacterial cell as compared to expression in a reference bacterial cell.

11. The isolated bacterial cell of embodiment 4, wherein the yqhC gene, yqhD gene, dkgA gene or any combination thereof is/are deleted in said bacterial cell.

12. The isolated bacterial cell of embodiment 4, wherein there is a change in the activity of the yqhD gene promoter or regulatory protein in said bacterial cell as compared to a reference bacterial cell.

13. The isolated bacterial cell of embodiment 4, wherein there is a change in the activity of the dkgA gene promoter or regulatory protein in said bacterial cell as compared to a reference bacterial cell.

14. The isolated bacterial cell of embodiment 4, wherein the level of YqhD, DkgA and/or YqhC protein is reduced in said bacterial cell due to the addition of an antisense RNA as compared to a reference bacterial cell.

15. The isolated bacterial cell of embodiment 4, wherein the level of YqhD, DkgA and/or YqhC protein is reduced in said bacterial cell due to the addition of an siRNA as compared to a reference bacterial cell.

16. The isolated bacterial, fungal or yeast cell of any preceding embodiment, wherein said bacterial, fungal or yeast cell further exhibits increased FucO activity, said FucO activity being increased by:
    a) expressing the FucO gene in a plasmid or a multicopy plasmid with a native promoter or a promoter sequence;
    b) integration of additional copies of the FucO gene within the chromosome of a bacterial, fungal or yeast cell;
    c) replacement of the FucO gene native promoter with a promoter that increases the level of gene expression in a bacterial cell; or
    d) mutation of the FucO enzyme to increase catalytic efficiency or reduce its Km.

17. An isolated bacterial, fungal or yeast cell having increased UcpA activity, wherein said bacterial, fungal or yeast cell is capable of producing a desired product, or has been genetically engineered to produce a desired product, and wherein said bacterial, fungal or yeast cell is prepared by a process comprising: a) growing a candidate mutant strain of the bacterial, fungal or yeast cell in the presence of furfural or 5-hydroxymethylfurfural (5-HMF); and b) selecting mutants that produce a desired product in the presence of about 5 mM to about 40 mM, about 5 mM to about 20 mM, about 15 to about 30 mM furfural and/or or 5-hydroxymethylfurfural (5-HMF), preferably about 15 mM furfural or about 15 mM to about 30 mM 5-HMF, and which exhibit increased UcpA activity or increased expression of ucpA mRNA.

18. The isolated bacterial, fungal or yeast cell of embodiment 17, wherein said cells are grown in the presence of furfural at concentrations of about 5 mM to about 40 mM, about 5 mM to about 20 mM, about 15 to about 30 mM, about 15 mM or about 15 mM to about 30 mM furfural.

19. The isolated bacterial, fungal or yeast cell of embodiment 17, wherein said cells are grown in the presence of 5-HMF at a concentration of about 5 mM to about 40 mM, about 5 mM to about 20 mM, about 15 to about 30 mM, about 15 mM or about 15 mM to about 30 mM 5-HMF.

20. The isolated bacterial, fungal or yeast cell of embodiments 17-19, wherein the selected mutants are compared to a reference bacterial, fungal or yeast cell for the ability to produce a desired product in the presence of furfural and/or or 5-hydroxymethylfurfural (5-HMF) and for increased expression of ucpA or ucpA mRNA.

21. A method of growing a bacterial, fungal or yeast cell comprising culturing a bacterial, fungal or yeast cell according to any one of embodiments 1-20 under conditions that allow for the growth of said bacterial, fungal or yeast cell.

22. A method for producing a desired product from a biomass, a hemicellulosic biomass, a lignocellulosic biomass, a cellulosic biomass or an oligosaccharide source comprising contacting the biomass, hemicellulosic biomass, lignocellulosic biomass, cellulosic biomass or oligosaccharide with the isolated bacterial, fungal or yeast cell according to any one of embodiments 1-20 and producing said desired product by fermenting said biomass, a hemicellulosic biomass, a lignocellulosic biomass, a cellulosic biomass or an oligosaccharide source in the presence of said bacterial, fungal or yeast cell.

23. The method of embodiment 21 or 22, wherein the bacterial, fungal or yeast cell produces a desired product, or has been genetically engineered to produce a desired product, selected from the group consisting of ethanol, lactic acid, succinic acid, malic acid, acetic acid, 1,3-propanediol, 2,3-propanediol, 1,4-butanediol, 2,3-butanediol, butanol, pyruvate, dicarboxylic acids, adipic acid and amino acids.

24. The method according to embodiment 21, 22 or 23, wherein said bacterial, fungal or yeast cell exhibits increased production of a desired product as compared to a reference bacterial, fungal or yeast cell in the presence of furfural and/or 5-hydroxymethylfurfural (5-HMF).

25. A method of increasing furfural and/or 5-hydroxymethylfurfural (5-HMF) resistance in a bacterial, fungal or yeast cell comprising increasing UcpA activity in said bacterial, fungal or yeast cell, as compared to a reference bacterial, fungal or yeast cell, wherein said bacterial, fungal or yeast cell having increased UcpA activity increases resistance of said bacterial, fungal or yeast cell to furfural and/or 5-hydroxymethylfurfural (5-HMF).

26. The method according to embodiment 25, wherein:
    a) expression of the yqhD gene is reduced in said bacterial cell as compared to a reference bacterial cell;
    b) expression of the dkgA gene is reduced in said bacterial cell as compared to a reference bacterial cell;
    c) expression of the yqhD gene, yqhC gene and/or the dkgA gene are reduced in said bacterial cell as compared to expression in a reference bacterial cell;
    d) expression of the yqhC gene is reduced in said bacterial cell as compared to expression in a reference bacterial cell;
    e) expression of the yqhD gene, the yqhC gene and the dkgA gene is reduced in said bacterial cell as compared to expression in a reference bacterial cell;
    f) the yqhD gene is not expressed or is deleted in said bacterial cell;
    g) the yqhD gene and the dkgA gene are not expressed or are deleted in said bacterial cell;
    h) the yqhC gene or yqhD gene, the yqhC gene and the dkgA gene are not expressed or are deleted in said bacterial cell;
    i) the yqhC gene is not expressed or is deleted in said bacterial cell;
    j) the dkgA gene is not expressed in said bacterial cell;
    k) the activity of the yqhD gene, yqhC gene and/or the dkgA gene product(s) are reduced in said bacterial cell as compared to expression in a reference bacterial cell; or
    l) the activity of the yqhC gene product is reduced in said bacterial cell as compared to expression in a reference bacterial cell.

27. The method according to embodiment 26, wherein the activity of YqhD protein is reduced in said bacterial cell as compared to a reference bacterial cell.

28. The method according to embodiment 26, wherein the activity of the YqhD protein and the activity of the DkgA protein in said bacterial cell are reduced in said bacterial cell as compared to a reference bacterial cell.

29. The method according to embodiment 26, wherein the activity of the YqhC protein is reduced in said bacterial cell as compared to a reference bacterial cell.

30. The method according to embodiment 26, wherein regulation of the expression of the yqhD gene is altered to reduce yqhD expression in said bacterial cell as compared to a reference bacterial cell.

31. The method according to embodiment 26, wherein regulation of the expression of the yqhD gene and regulation of expression of the dkgA gene are altered to reduce yqhD and dkgA expression in said bacterial cell as compared to expression in a reference bacterial cell.

32. The method according to embodiment 26, wherein regulation of expression of the yqhC gene is altered to reduce yqhC expression in said bacterial cell as compared to expression in a reference bacterial cell.

33. The method according to embodiment 26, wherein the yqhC gene, yqhD gene, dkgA gene or any combination thereof is/are deleted.

34. The method according to embodiment 26, wherein there is a change in the activity of the yqhD gene promoter or regulatory protein in said bacterial cell as compared to a reference bacterial cell.

35. The method according to embodiment 26, wherein there is a change in the activity of the dkgA gene promoter or regulatory protein in said bacterial cell as compared to a reference bacterial cell.

36. The method according to embodiment 26, wherein the level of YqhD, DkgA and/or YqhC protein is reduced in said bacterial cell due to the addition of an antisense RNA as compared to a reference bacterial cell.

37. The method according to embodiment 26, wherein the level of YqhD, DkgA and/or YqhC protein is reduced in said bacterial cell due to the addition of an siRNA as compared to a reference bacterial cell.

38. The method according to any one of embodiments 25-37, further comprising increasing FucO activity in said bacterial, fungal or yeast cell, said FucO activity being increased by:
  a) expressing the FucO gene in a plasmid or a multicopy plasmid with a native promoter or a promoter sequence;
  b) transposon integration of additional copies of the FucO gene within the chromosome of a bacterial, fungal or yeast cell;
  c) replacement of the FucO gene native promoter with a promoter that increases the level of gene expression in a bacterial, fungal or yeast cell; or
  d) mutation of the FucO enzyme to increase catalytic efficiency or reduce its Km.

39. The method according to embodiment 25, wherein said bacterial, fungal or yeast cell is prepared by a process comprising: a) growing a candidate mutant strain of the bacterial, fungal or yeast cell in the presence of furfural or 5-hydroxymethylfurfural (5-HMF); and b) selecting mutants that produce a desired product in the presence of furfural and/or 5-hydroxymethylfurfural (5-HMF).

40. The method according to embodiment 39, wherein said cell is grown in the presence of furfural.

41. The method according to embodiment 39, wherein said cell is grown in the presence of 5-HMF.

42. The method according to any one of embodiments 39-41, wherein the selected mutants are compared to a reference bacterial, fungal or yeast cell for the ability to produce a desired product in the presence of furfural and/or or 5-hydroxymethylfurfural (5-HMF).

43. The isolated bacterial cell or method according to any one of embodiments 1-42, wherein said bacterial cell is a Gram-negative or a Gram-positive bacterial cell.

44. The isolated bacterial cell or method according to embodiment 43, wherein the Gram-negative bacterial cell is a bacterial cell selected from the genera of *Escherichia, Zymomonas, Acinetobacter, Gluconobacter, Geobacter, Shewanella, Salmonella, Enterobacter* or *Klebsiella* and the Gram-positive bacteria is a bacterial cell selected from the genera of *Bacillus, Clostridium, Corynebacterial* cell, *Lactobacillus, Lactococcus, Oenococcus, Streptococcus* and *Eubacterial* cell.

45. The isolated bacterial cell or method according to embodiment 44, wherein the bacterial cell is *Escherichia coli* or *Klebsiella oxytoca*.

46. The isolated bacterial cell or method according to embodiment 43, wherein said bacterial cell is selected from *Thermoanaerobes, Bacillus* spp., *Paenibacillus* spp. or *Geobacillus* spp.

47. The isolated yeast cell or method according to any one of embodiments 1-42, wherein said yeast cell is a *Candida, Hansenula, Kluyveromyces, Pichia, Saccharomyces, Schizosaccharomyces,* or *Yarrowia* cell.

48. The isolated yeast cell or method according to embodiment 47, wherein said yeast cell is *Kluyveromyces lactis, Saccharomyces carlsbergensis, Saccharomyces cerevisiae, Saccharomyces diastaticus, Saccharomyces douglasii, Saccharomyces kluyveri, Saccharomyces norbensis, Saccharomyces oviformis,* or *Yarrowia lipolytica*.

49. The isolated fungal cell or method according to embodiments 1-42, wherein said fungal cell is a *Acremonium, Aspergillus, Aureobasidium, Bjerkandera, Ceriporiopsis, Chrysosporium, Coprinus, Coriolus, Cryptococcus, Filibasidium, Fusarium, Humicola, Magnaporthe, Mucor, Myceliophthora, Neocallimastix, Neurospora, Paecilomyces, Penicillium, Phanerochaete, Phlebia, Piromyces, Pleurotus, Schizophyllum, Talaromyces, Thermoascus, Thielavia, Tolypocladium, Trametes,* or *Trichoderma* cell.

50. The isolated fungal cell or method according to embodiment 49, wherein said fungal cell is an *Aspergillus awamori, Aspergillus foetidus, Aspergillus fumigatus, Aspergillus japonicus, Aspergillus nidulans, Aspergillus niger, Aspergillus oryzae, Bjerkandera adusta, Ceriporiopsis aneirina, Ceriporiopsis caregiea, Ceriporiopsis gilvescens, Ceriporiopsis pannocinta, Ceriporiopsis rivulosa, Ceriporiopsis subrufa, Ceriporiopsis subvermispora, Chrysosporium inops, Chrysosporium keratinophilum, Chrysosporium lucknowense, Chrysosporium merdarium, Chrysosporium pannicola, Chrysosporium queenslandicum, Chrysosporium tropicum, Chrysosporium zonatum, Coprinus cinereus, Coriolus hirsutus, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides, Fusarium venenatum, Humicola insolens, Humicola lanuginosa, Mucor miehei, Myceliophthora thermophile, Neurospora crassa, Penicillium purpurogenum, Phanerochaete chrysosporium, Phlebia radiata, Pleurotus eryngii, Thielavia terrestris, Trametes villosa, Trametes versicolor, Trichoderma harzianum, Trichoderma koningii, Trichoderma longibrachiatum, Trichoderma reesei,* or *Trichoderma viride* cell.

51. The isolated bacterial, fungal or yeast cell according to any one of embodiments 1-20 or 43-50, wherein said bacterial, fungal or yeast cell produces a desired product in the presence of about 5 mM to about 40 mM, about 5 mM to about 20 mM, about 15 mM to about 30 mM, or about 15 mM furfural and/or 5-HMF.

52. The isolated bacterial, fungal or yeast cell according to any one of embodiments 1-20 or 43-50, wherein said bacterial, fungal or yeast cell expresses increased amounts of a UcpA polypeptide comprising SEQ ID NO: 1.

53. The isolated bacterial, fungal or yeast cell according to any one of embodiments 1-20 or 43-50, wherein said bacterial, fungal or yeast cell expresses increased amounts of an mRNA encoding a UcpA polypeptide.

54. The isolated bacterial, fungal or yeast cell according to any one of embodiments 1-20 or 43-50, wherein said bacterial, fungal or yeast cell expresses increased amounts of an mRNA encoding a UcpA polypeptide comprising SEQ ID NO: 1.

The terms comprise, comprises, comprising, having and containing are open-ended terms and can be used interchangeably with consisting, consists or consisting essentially of throughout the subject application and claims.

All patents, patent applications, provisional applications, and publications referred to or cited herein are incorporated by reference in their entirety, including all figures and tables, to the extent they are not inconsistent with the explicit teachings of this specification.

Following are examples which illustrate procedures for practicing the invention. These examples should not be construed as limiting. All percentages are by weight and all solvent mixture proportions are by volume unless otherwise noted.

Example 1

Alteration of UcpA Activity for the Production of a Desired Product

Materials and Methods
Strains, Media and Growth Conditions

Strains, plasmids and primers used in this study are listed in Table 1. All constructions were verified by DNA sequencing. Strain LY180 was previously engineered for ethanol production (Miller et al., 2009a). Strain KJ122 was previously engineered for succinate production (Jantama et al., 2008; Zhang et al., 2009).
Comparison of mRNA Levels Before and after Addition of 15 mM Furfural Analysis of mRNA as a measure of gene expression was performed as previously described (Miller et al., 2009a). Cultures were grown using 4 separate 500-ml fermentation vessels per strain. Initial samples (control) were removed for RNA extraction when the culture density reached approximately 0.66 g dry cell weight (dcw) liter$^{-1}$ (1.5 OD 550 nm). Furfural (15 mM) was then added and incubation continued. After 15 min incubation with furfural, cells were harvested for RNA extraction. RNA was submitted to NimbleGen for analysis of global expression. Expression data was further analyzed using ArrayStar and Excel.
Furfural Toxicity and Furfural Reduction In Vivo Furfural toxicity was measured in tube cultures (13 mm by 100 mm) containing 4 ml of AM1 medium with 50 g liter$^{-1}$ xylose, 12.5 mg liter$^{-1}$ ampicillin, furfural, and other supplements as indicated (Miller et al., 2009a, b). Cultures were inoculated to an initial density of 22 mg dcw liter$^{-1}$. IPTG (0.1 mM) was included for fucO induction. Cell mass was measured at 550 nm after incubation for 48 h (37° C.). For cysteine supplement experiment, the culture condition was the same but included 0.1 mM cysteine as an amendment.

Furfural toxicity was measured in a similar manner using KJ122 (succinate production). For this strain, the medium also included 100 mM MOPS (pH 7.0) and 100 mM KHCO$_3$.

In vivo furfural reduction was measured during incubation in AM1 medium containing 10 mM furfural and 50 g liter$^{-1}$ xylose. Cells were pre-incubated with chloramphenicol (40 mg liter$^{-1}$) for 1 h to arrest growth (0.88 mg dcw cells ml$^{-1}$), prior to the addition of furfural. Furfural concentration was measured as previously described using a Beckman spectrophotometer DU800 (Martinez et al., 2000b).
Assays for Furfural and 5-HMF Reductase Activity Cultures were grown overnight to a cell density of approximately 0.66 mg dcw ml$^{-1}$ (37° C.) in closed tubes containing 20 ml AM1 (50 g liter$^{-1}$ xylose, 0.1 mM IPTG and 12.5 mg liter$^{-1}$ ampicillin). Cells were harvested by centrifugation (7,000 g for 5 min, 4° C.), washed twice with 10 ml of cold sodium phosphate buffer (50 mM pH 7.0), resuspended to a cell density of 4.4 mg dcw ml$^{-1}$, and disrupted in buffer containing 1 mM dithiothreitol using a Fastprep-24 (MP Biomedicals, Solon, Ohio). After clarification at 13,000 g (10 min, 4° C.), protein concentration was determined using a BCA™ Protein Assay Kit (Thermo Scientific, Rockford, Ill.). Furfural-dependent reduction was measured using NADH and NADPH by monitoring the decrease in absorbance at 340 nm (extinction coefficient of NADH of 6,220 M$^{-1}$ cm$^{-1}$; extinction coefficient of NADPH of 6,020 M$^{-1}$ cm$^{-1}$). Reaction mixtures contained 200 mM phosphate buffer (pH 7.0), 10 mM furfural, and 0.2 mM NADH or NADPH. NADH-dependent and NADPH-dependent reduction of 5-HMF (10 mM) was measured in a similar fashion.

Additional compounds (ethanol, glycerol, n-butanol, 2-propanol, methanol, acetoin, diacetyl, methyglyoxal, dihydroxyacetone, acetaldehyde, and 1,3-propandiol) were tested as potential substrates for UcpA using appropriate cofactors. No alcohol dehydrogenase, aldehyde reductase or acetaldehyde dehydrogenase activity was found. None of the substrates was metabolized at a higher rate by cell lysates from ucpA-induced LY180 (pLOI4856) than by control lysates from LY180 containing an empty vector.
Assay for Pyridine Nucleotide Transhydrogenase Activity Cultures were grown overnight to a cell density of approximately 0.66 mg dcw ml$^{-1}$ (37° C.) in closed tubes containing 20 ml AM1 (50 g liter$^{-1}$ xylose, 0.1 mM IPTG and 12.5 mg liter$^{-1}$ ampicillin). Cells were harvested by centrifugation (7,000 g for 5 min, 4° C.), washed twice with 10 ml of cold Tris-HCl buffer (50 mM pH 7.0), resuspended to a cell density of 4.4 mg dcw ml$^{-1}$, and disrupted in the same buffer using a Fastprep-24 (MP Biomedicals, Solon, Ohio). Transhydrogenase activity was determined in cell extract without centrifugation as previously described (Sauer et al., 2004; Park et al., 1997). Reaction mixtures contained 50 mM Tris-HCl buffer (pH 7.0), 2 mM MgCl$_2$, 0.5 mM NADPH and 1 mM 3-acetylpyridine adenine dinucleotide (AcPy-NAD$^+$) and 20-100 µg crude cell extract. Transhydrogenase activity was determined by the absorbance increase of AcPy-NADH at 375 nm and the molar extinction coefficient of AcPy-NADH used was 9020 M$^{-1}$ cm$^{-1}$ (Park et al., 1997).
Protein Analysis Using SDS-PAGE Gels Cell lysates (20 µg protein per lane) were analyzed using a 15% SDS-polyacrylamide gel and stained with Coomassie Blue as previously described (Miller et al., 2009b).
Effect of ucpA Expression on Fermentation Seed pre-cultures of strains containing pTrc99A or pLOI4856 were grown from plates using sealed culture tubes containing AM1 medium (20 g liter$^{-1}$ xylose, 12.5 mg liter$^{-1}$ ampicillin). After incubation for 16 h, pre-inocula were diluted into 500-ml fermentation vessels containing 300 ml AM1 media (100 g liter$^{-1}$ xylose, 1 mM betaine, 0.1 mM IPTG, 12.5 µg ml$^{-1}$ ampicillin) to provide a starting density of 13.2 mg dcw. After 24 h growth, these seed cultures were used to provide a starting inoculum for batch fermentations (AM1 medium, 100 g liter$^{-1}$ xylose, 12.5 µg ml$^{-1}$ ampicillin, 0.1 mM IPTG, 13.2 mg dcw initial density, and furfural). Fermentations were maintained at pH 6.5 ethanol by the automatic addition of KOH as previously described (Miller et al., 2009b). Ethanol was measured using an Agilent 6890N gas chromatograph (Palo Alto, Calif.) equipped with a flame ionization detector and a 15-meter HP-Plot Q Megabore column. Furfural concentration was monitored using a Beckman DU spectrophotometer (Martinez et al., 2000b; Miller et al., 2009b). Organic acids and xylose were measured by high-performance liquid chromatography (Miller et al., 2009b).

Results:

Discovery that UcpA Expression can Increase Furfural Tolerance

We have previously shown that a NADH-dependent oxidoreductase encoded by the native *E. coli* fucO gene has furfural reductase activity and increases furfural tolerance. Based on this success, we initiated studies to identify additional NADH oxidoreductases that would confer increased furfural tolerance using expression arrays that examine the entire genome response to added furfural. This approach failed to identify additional NADH-dependent furfural reductase genes that confer furfural tolerance.

Figure 2:
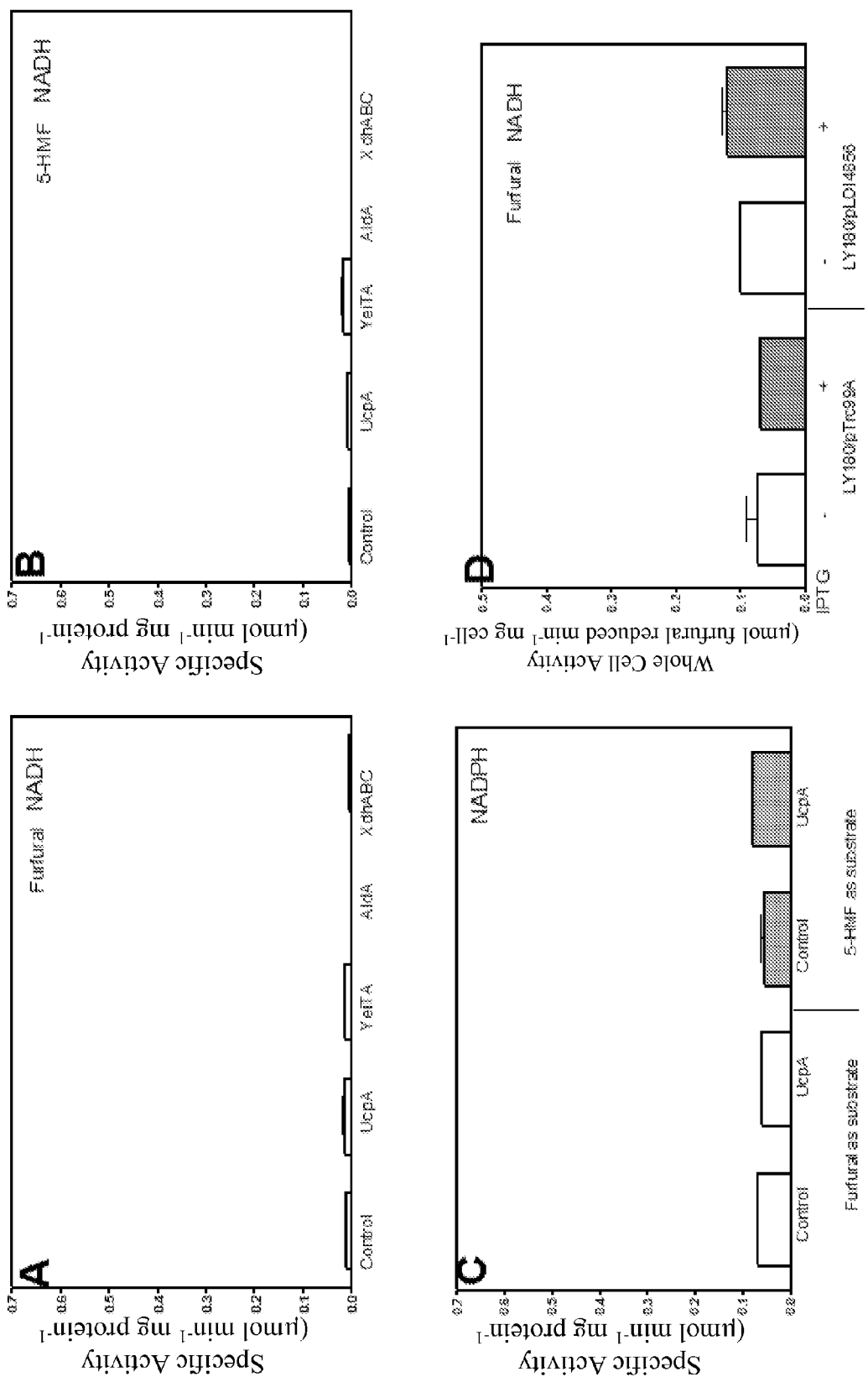
FIGS. 2A-2D. Furfural reductase activities for UcpA, YeiTA, AldA and XdhABC.

In the course of these investigations, however, we made the unexpected discovery of a novel gene (ucpA) that confers furfural tolerance by an unknown mechanism. Although UcpA has a putative NAD(P)H-binding site and shares some similarity with short chain oxidoreductases, there is no literature that demonstrates any enzymatic activity with this protein (Sirko et al., 1997). We have found that UcpA does not encode furfural reductase activity based on in vitro assays and whole cell (in vivo) assays despite overexpression on protein gels (FIG. 2). The mechanism by which expression of UcpA causes an increase in furfural tolerance is unknown.

There is only a single paper published concerning the ucpA gene and no known function (Sirko et al., 1997). UcpA was identified as being part of a monocistronic operon and is proposed to be under the control of several transcription factors (Crp, FruR, and IHF). This gene was named simply based on chromosomal location, upstream of the cysP operon.

UcpA was discovered accidentally as a beneficial gene for furfural tolerance during a search for *E. coli* NADH-utilizing oxidoreductase genes that could reduce furfural and confer resistance. This gene has similarities to other oxidoreductases but did not encode a furfural reductase activity. We began by comparing expression levels of all *E. coli* genes in the absence of furfural and in the presence of 15 mM furfural (Table 1). These were then sorted to identify only known or putative oxidoreductases that exhibited a 3-fold or greater increase in expression level (Table 2). These were further sorted to identify 5 candidate oxidoreductases that are known or putative users of NADH and have a 3-fold or higher expression level in the presence of 15 mM furfural. One of the genes was fucO, a gene previously discovered to reduce furfural using NADH and to increase furfural tolerance in *E. coli*. Four new candidates were identified. Two were operons encoding subunits (xdhABC and YeiTA) and two were monocistronic (ucpA and aldA). These 4 candidates are shown in bold type in Table 2.

Expression of ucpA Increased Furfural Tolerance in Tube Culture Assays

Figure 1B:
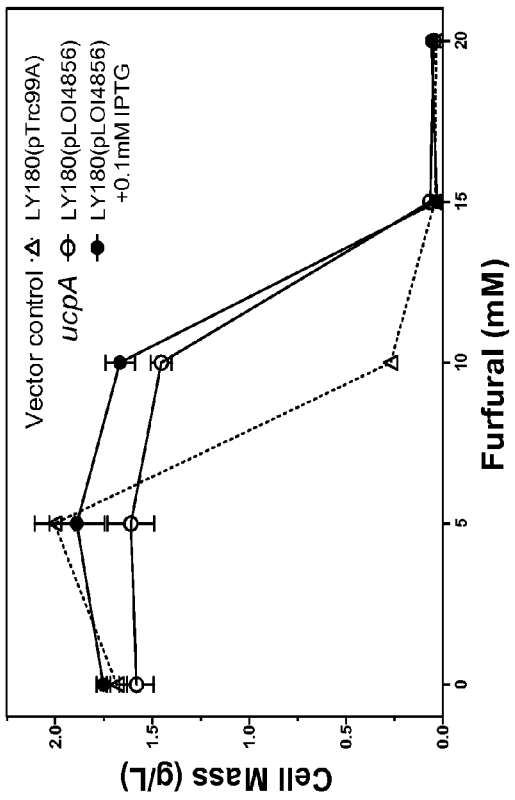
Figure 1C:
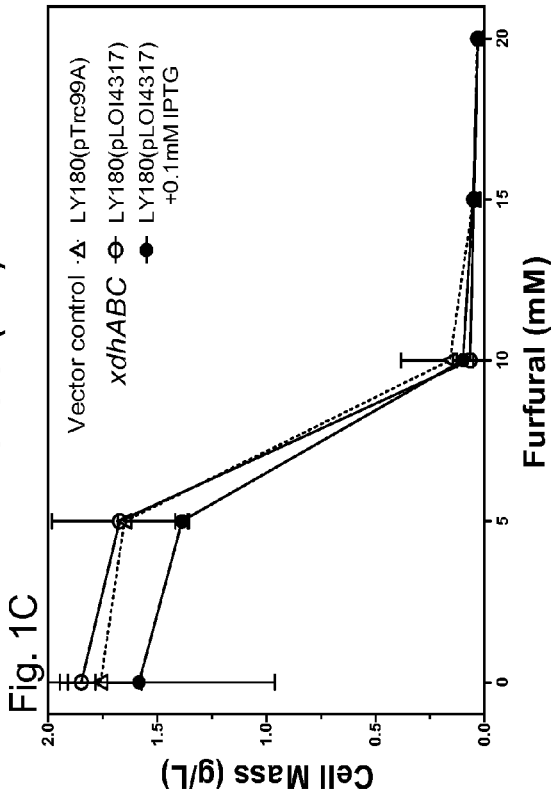
Figure 1D:
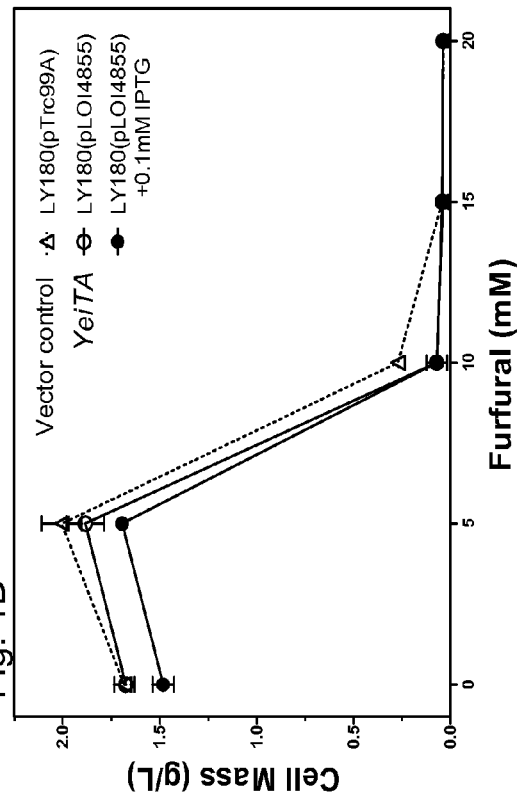

The mRNA levels of oxidoreductases UcpA, YeiTA, AldA, XdhABC were increased by more than 3-fold in ethanologenic *E. coli* LY180 upon 15 mM furfural addition. To test whether overexpression of these candidate genes increased furfural tolerance, the growth inhibition of LY180 by furfural was measured with IPTG-induced expression of these genes on plasmids (FIG. 1). Only IPTG-induced expression of ucpA in LY180 (pLOI4856) increased the furfural tolerance and the minimum inhibitory concentration. Expression of ucpA increased tolerance by 50%, from 10 mM furfural to 15 mM furfural (FIG. 1B). LY180 (pLOI4856) exhibited improved furfural tolerance from leaky expression from TRC promoter on the plasmid without IPTG induction (FIG. 1). The other three candidates were no better than the vector alone at increasing furfural tolerance.

Figure 3:
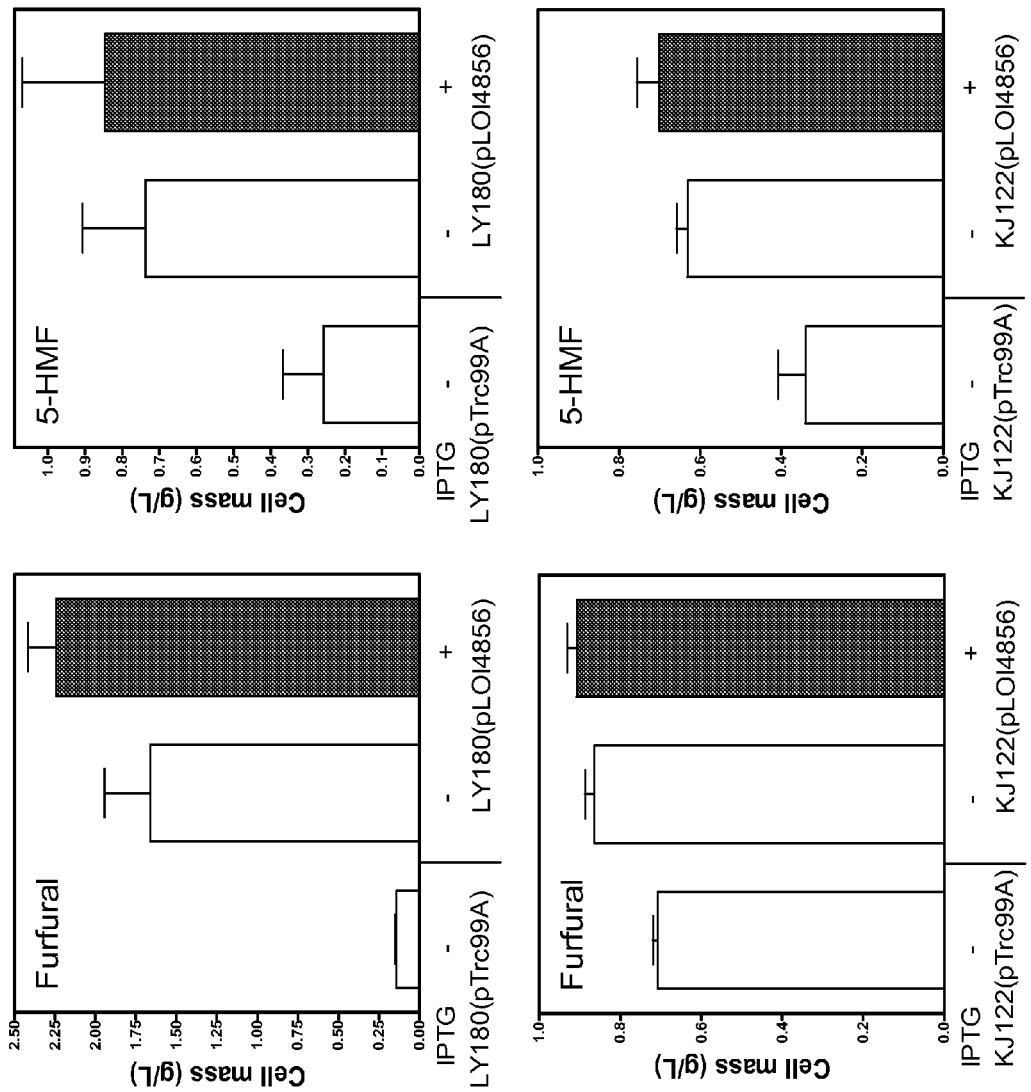
FIGS. 3A-3D. Effect of ucpA induction on furan tolerance in LY180 (ethanol) and KJ122 (succinate). Cultures were tested with 10 mM furfural (LY180), 5 mM furfural (KJ122), and 15 mM 5-HMF (both strains). Solid bars indicate induction by IPTG.

Expression of ucpA was also shown to increase resistance to HMF (FIGS. 3A and 3B). The beneficial effect of ucpA expression was not limited to LY180 (ethanol production from xylose) and could also be transferred to KJ122, a biocatalyst for succinate production (FIGS. 3C and 3D). The remaining three candidate genes were no better than the empty vector and were not pursued further.

Figure 5A:
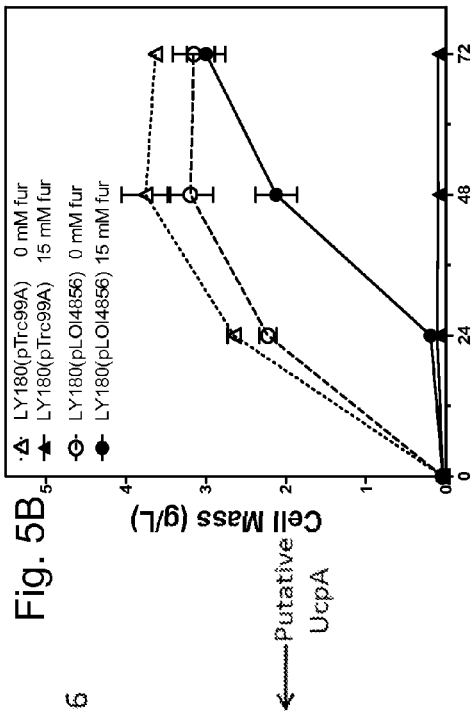
FIGS. 5A-5D. Effect of ucpA expression on furfural tolerance during ethanol production from xylose.
Figure 5B:
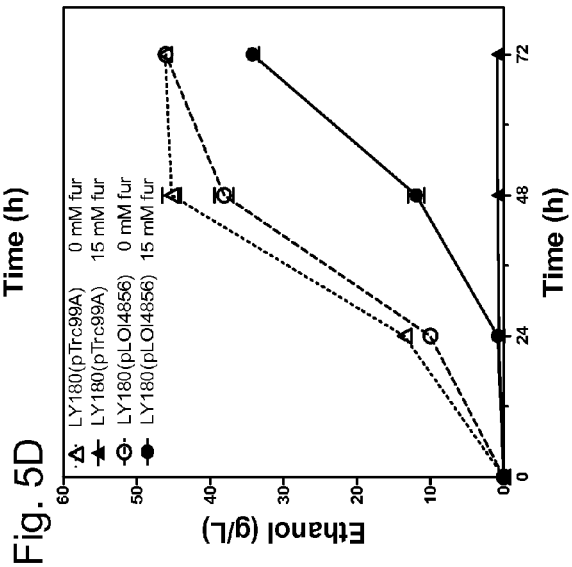
Figure 5C:
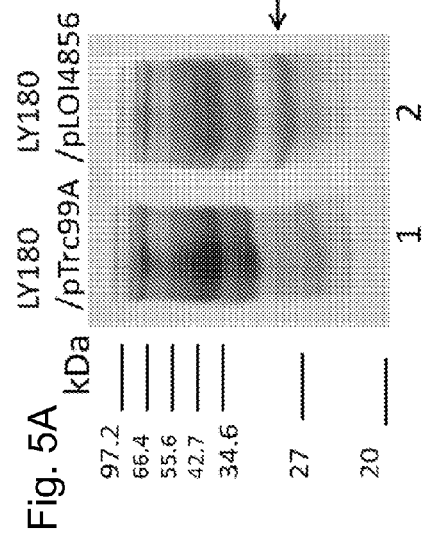
Figure 5D:
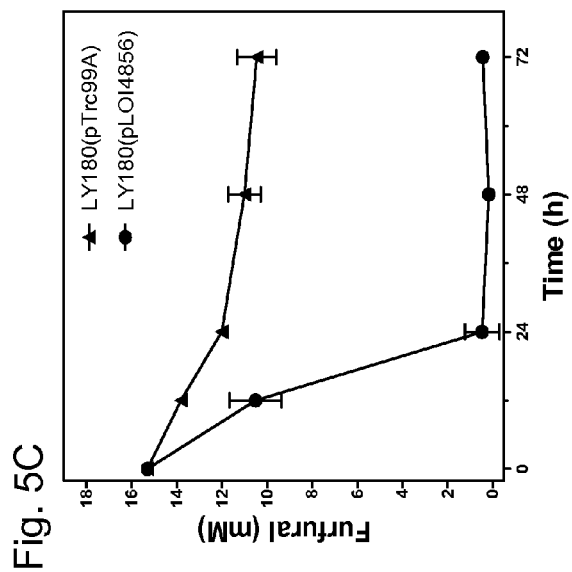

Furan Reductase Activity in Cells with Overexpression of ucpA, yeiTA, aldA, xdhABC The genes ucpA, yeiTA, aldA, and xdhABC were cloned (pLOI4856, pLOI4855, pLOI4320 and pLOI4317, respectively) and transformed into LY180. Cell lysates were compared to LY180 with vector alone (FIGS. 2A and 2B). Control lysates with vector exhibited low levels of NADPH-dependent furan reductase activity for both furfural and 5-HMF, and even lower levels of NADH-dependent activity (FIGS. 2A, 2B and 2C). IPTG-induced expression of ucpA, yeiTA, aldA, xdhABC did not result in an increase in NADH-dependent furfural or 5-HMF reductase activity (FIGS. 2A and 2B). No increase in NADPH-dependent or NADH-dependent furfural or 5-HMF reductase activity was detected when cells overexpressed ucpA (FIG. 2C), although induced expression was clearly evident on SDS-PAGE gels (FIG. 5A). Similarly, IPTG-induced expression of ucpA in LY180 (pLOI4856) did not increase the in vivo specific activity (whole cell) for furfural reduction as compared to the control strain, LY180 (pTrc99A) containing empty vector (FIG. 2D). Expression of ucpA increased furfural resistance to LY180, suggesting that UcpA is not a furfural reductase.

Additional compounds (ethanol, glycerol, n-butanol, 2-propanol, 1,3-propandiol, methanol, acetoin, diacetyl, methylglyoxal, dihydroxyacetone, and acetaldehyde) were tested as substrates for UcpA. However, none appeared to be metabolized. Activities for induced LY180 (pLOI4856) were no higher than for the empty vector control.

Pyridine Nucleotide Transhydrogenase Activity in Cells with Overexpression of ucpA Our previous results showed that overexpression of pyridine nucleotide transhydrogenase pntAB at some level makes cells more furan resistant (Miller et al., 2009a; Miller et al., 2010). Cell lysates of LY180 with pLOI4856 or empty vector were obtained after induced overexpression of ucpA by IPTG. Overexpression of ucpA did not alter the transhydrogenase activity in LY180, suggesting that the furan resistant effect of UcpA is not due to increased pyridine nucleotide transhydrogenase activities.

Figure 4:
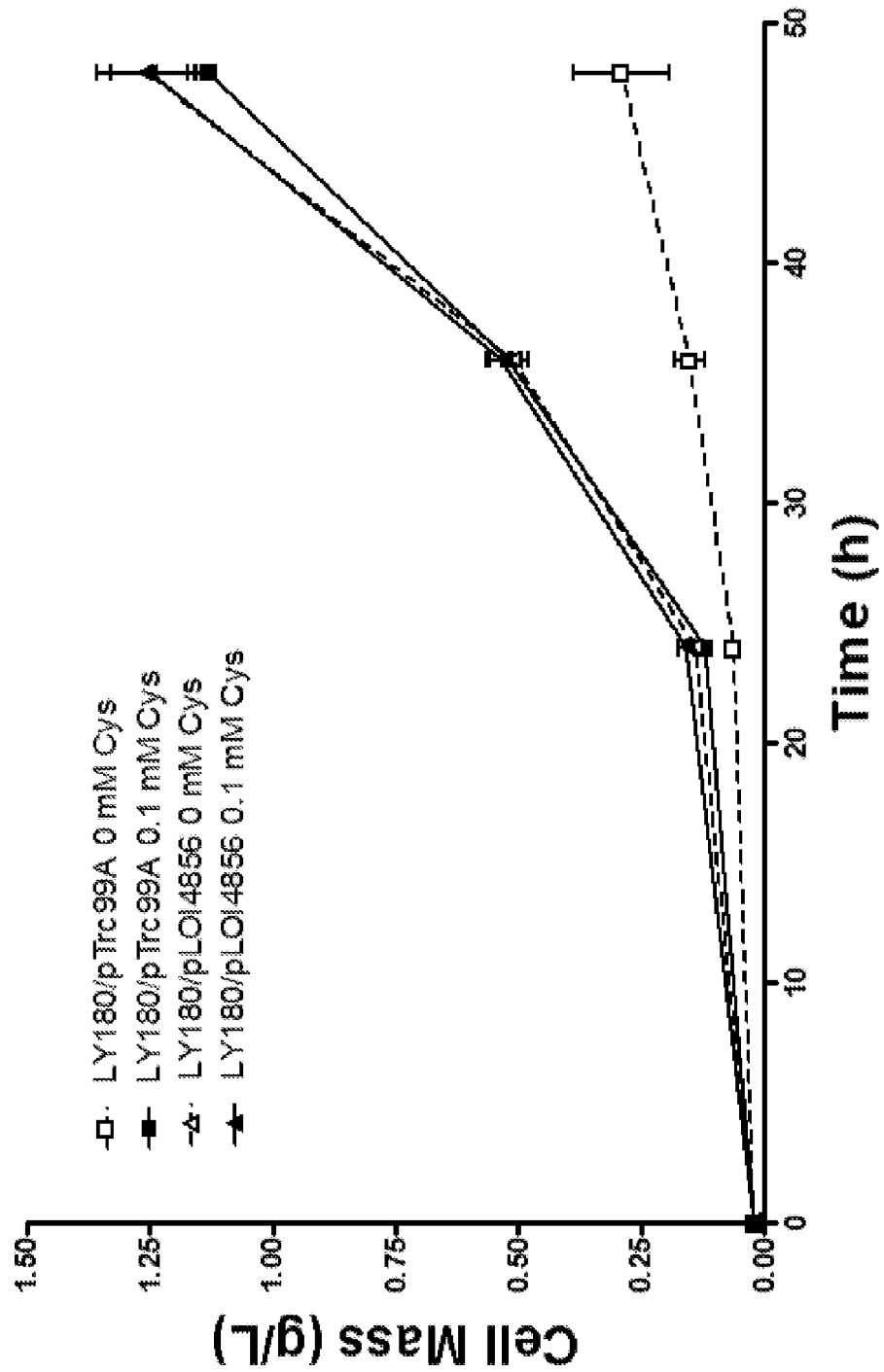
FIG. 4. Effects of media supplements and ucpA expression on furfural tolerance. Strains LY180(pTrc99A) and LY180 (pLOI4856) were grown in tube cultures containing AM1 medium 50 g liter$^{-1}$ xylose, 1.0 g liter$^{-1}$ furfural, 0.1 mM IPTG, 0 or 0.1 mM L-cysteine. Growth without cysteine supplements was indicated by open symbols and dotted lines. Growth in the presence of cysteine was indicated by closed symbols and solid lines.

Cysteine Supplement Did not Increase Furfural Resistance in Cells with Overexpression of ucpA Our previous studies have shown the primary cause for growth inhibition by low concentrations of furfural in LY180 is the process of furfural reduction by YqhD competitively draining the biosynthetic pools of NADPH and limiting sulfur assimilation (Miller et al., 2009a, b). Furfural tolerance can be increased by the addition of cysteine to decrease biosynthetic demand for NADPH. LY180 with a control vector (pTrc99A) showed growth inhibition in the presence of 10 mM furfural and cell growth was increased by supplementing with 0.1 mM L-cysteine in the media (FIG. 4). However, the addition of L-cysteine did not alter the growth of the strain LY180 (pLOI4856) when ucpA was induced in the presence of 10 mM furfural, suggesting sulfur assimilation was not limited when cells overexpressed ucpA. Although the mechanism is unknown, the ucpA gene product could be involved in more efficient sulfur assimilation or have some role in the interconversion of NADH and NADPH.

Expression of ucpA Increased Ethanol Production in the Presence of Furfural

The effect of ucpA expression on furfural tolerance was examined during batch fermentations of xylose to ethanol (FIG. 5). Strain LY180 (pTrc99A) was unable to grow in the presence of 15 mM furfural. After a 24-h lag during which most of the furfural was metabolized, LY180 (pLOI4856) began to grow and ferment xylose to ethanol. Expression of ucpA in LY180 (pLOI4856) increased the rate of furfural metabolism, decreased the growth lag, and increased the rate of xylose fermentation to ethanol. Ethanol production with furfural was improved by expression of ucpA, LY180 (pLOI4856); however, longer fermentation times were required as compared to control strains without furfural. Final ethanol yields (100 g liter$^{-1}$ xylose) for LY180 (pLOI4856) with furfural (15 mM) were similar to those for strains without furfural, approximately 90% of the theoretical maximum.

SDS-PAGE Confirming Expression of ucpA in LY180

The expression of ucpA was also examined using SDS-PAGE (FIG. 5A). Protein lysates of IPTG-induced LY180 (pLOI4856) contained a new band in the region corresponding to the predicted size for UcpA (27.85 kD).

Effects of UcpA on Growth, Ethanol Production, and Furfural Metabolism

Figure 6B:
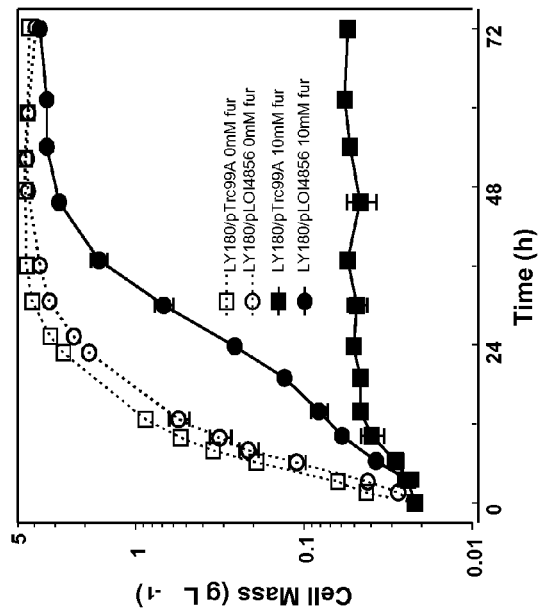
FIGS. 6A-6D. Plasmid expression of ucpA increases furfural tolerance (MIC) and ethanol production by LY180 (pH-controlled fermentations; 10% xylose).

Derivatives of LY180 containing these plasmids were tested for furfural tolerance with (0.1 mM IPTG) and without IPTG induction using an MIC assay (Miller et al., 2009a; Miller et al., 2010; Wang et al., 2011b). Only pLOI4856 (ucpA) was beneficial (FIG. 6A), increasing the MIC of furfural by 50% (15 mM) as compared to the vector control and the three other constructs (10 mM). IPTG provided little further benefit indicating that high levels of UcpA are not needed. Expression of ucpA in LY180 (pLOI4856) also increased the MIC for 5-HMF from 16 mM for the control to 20 mM for LY180 (pLOI4856) (data not shown).

The effects of UcpA on growth, ethanol production, and furfural metabolism were investigated in more detail during pH-controlled batch fermentation in mineral salt medium (AM1 medium containing 100 g xylose liter$^{-1}$, 0.1 mM IPTG and 12.5 µg ml$^{-1}$ ampicillin for all cultures harboring plasmids; furfural as indicated; inoculum of 22 mg dcw liter$^{-1}$) as previously described (Wang et al., 2011b). Ethanol (retention time 1.1 min) and furfuryl alcohol (retention time 6.2 min) were measured using an Agilent 6890N gas chromatograph (Santa Clara, Calif.) (Miller et al., 2009b). Furoic acid (retention time of 51.2 min) and sugars were measured by high-performance liquid chromatography (Geddes et al., 2010a). Furfural was measured using a Beckman-Coulter DU 800 spectrophotometer (Martinez et al., 2000a).

Figure 6D:
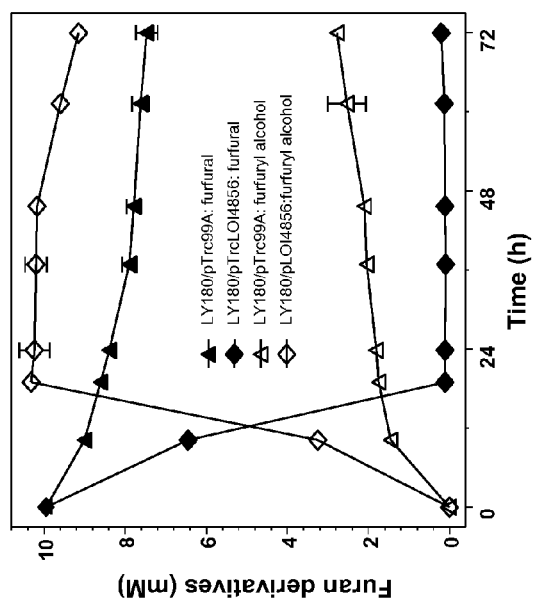
Figure 6A:
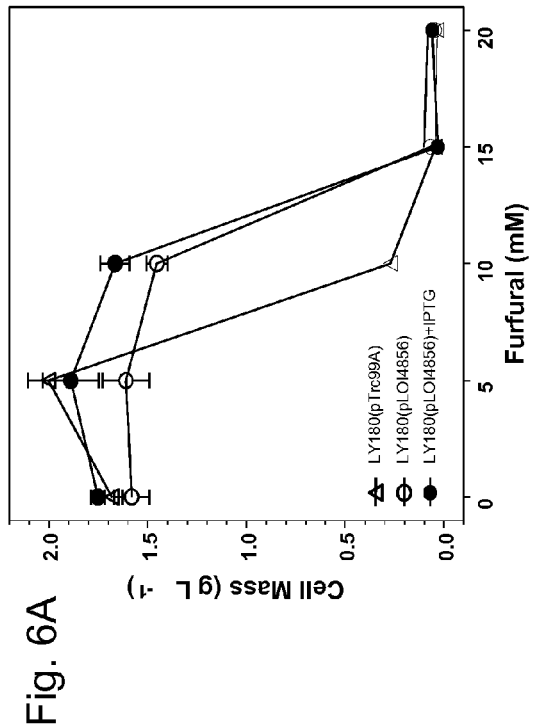
Figure 6C:
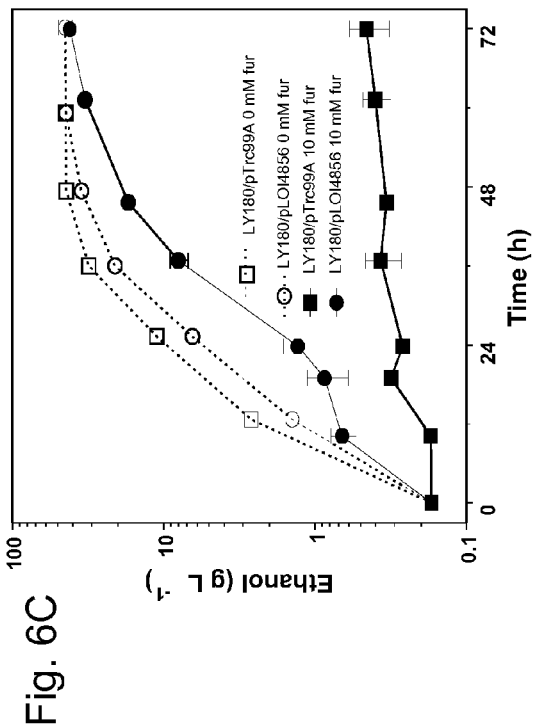

Plasmid pLOI4856 containing ucpA increased furfural tolerance for growth and ethanol production in LY180 as compared to the control containing pTrc99A (FIGS. 6B and 6C),
with IPTG induction. The vector control was substantially inhibited by 10 mM furfural for over 72 h (Table 3), while only a modest initial inhibition was observed for LY180 (pLOI4856). During the initial slow phase, LY180 (pLOI4856) quantitatively converted furfural to the less toxic furfuryl alcohol (FIG. 6D). No furoic acid was detected. Ethanol production and growth followed similar trends. After furfural was metabolized, the rate of growth and ethanol production increased to near that of controls without furfural with similar final yields for cell mass and ethanol.

UcpA appears to increase growth in the presence of furfural but does not directly metabolize furfural using NADH or NADPH as electron donors. Although the volumetric rate of furfural reduction was increased by plasmid copies of ucpA (FIG. 6D), whole-cell specific activity (furfural reductase; Wang et al., 2011b) was similar to the vector control (<0.10 U mg dcw$^{-1}$). Deletion of chromosomal ucpA in an LY180 background (strain XW118) using Red recombinase technology (5; Gene Bridges GmbH, Dresden, Germany) decreased furfural tolerance (FIG. 7; Table 3), confirming that the chromosomally encoded UcpA is functional and beneficial.

Strain LY180 has been highly engineered for ethanol production and contains many mutations. Although this engineered strain was more sensitive to inhibition by furfural than the parent strain W, cell yields for LY180 were twice that of strain W with 0 mM and 8 mM furfural (Table 3). Both LY180 and strain W exhibited similar changes in furfural tolerance with regard to ucpA. The addition of plasmid pLOI4856 increased furfural tolerance in strain W (Table 3). Deletion of ucpA from strain W (strain XW137) lowered furfural tolerance. The furfural sensitivity of LY180 may be related to higher aldehyde levels in this homoethanol producer, as compared to strain W (mixed acid fermentation). Mixtures of acetaldehyde and furfural were previously shown to exhibit more than additive toxicity for ethanologenic *E. coli* (Zaldivar et al., 1999).

Discussion

Furfural, the dehydration product of pentose sugars, is an important microbial inhibitor that is formed during dilute acid hydrolysis of hemicelluloses (Almeida et al., 2009; Milles et al., 2009). Diverse approaches have been explored for furfural removal such as lime addition (pH 10) (Almeida et al., 2009; Martinez et al., 2001; Martinez et al., 2000a) and the selection of resistant mutants (Almeida et al., 2009; Liu et al., 2006; Miller et al., 2009b). Developing biocatalysts that are more furfural tolerant would be helpful for the production of renewable products from inedible feedstocks.

Furfuryl alcohol is known to be less toxic than furfural (Zaldivar et al., 2000; Zaldivar et al., 1999). Thus an effective microbial furfural reduction system has the potential to increase furfural resistance. Furfural-resistant strains of *S. cerevisiae* have been isolated (Almeida et al., 2008; Laadan et al., 2008; Liu et al., 2009; Liu et al., 2008) and found to exhibit increased expression of aldehyde reductases that may contribute to tolerance. However, the previously reported furfural reductases such as YqhD in *E. coli* have been attributed to an unusually low Km for NADPH (8 µM), starving essential biosynthetic reactions by depletion of the NADPH pool during the furfural reduction process (Miller et al., 2009a, b). Many oxidoreductases were also induced in a furfural resistant mutant (EMFR9) in comparison to the parent, but none were found to reduce toxicity when overexpressed in the parent strain (Miller et al., 2009a, b). Here, we tested known and putative oxidoreductase genes that were induced by furfural addition, none of which showed furfural reductase activity. Surprisingly, one of these (ucpA) was quite effective for improving furfural tolerance, although the mechanism has yet to be defined.

The discovery of the detoxification effect of ucpA appears to offer a new route for improving furfural tolerance. The approaches improving NADPH availability such as cysteine addition also increase 5-HMF tolerance in LY180, suggesting overexpression of ucpA should also increase 5-HMF tolerance. Overexpression of ucpA provides a detoxification strategy that may be generally useful for other microbial catalysts and various products when using lignocellulosic sugars or sugar streams containing furan aldehydes. Our studies have demonstrated the utility of this approach for ethanol production using engineered strains of E. coli (FIG. 5). An analogous strategy that minimizes the depletion of NADPH pools during the detoxification process may be generally useful for other toxic agents in lignocellulosic sugar streams and with other organisms.

Plasmid expression of ucpA was beneficial for both the native W strain and ethanologenic strain LY180. Homologues of UcpA are widely distributed in nature (Guo et al., 2006; Sirko et al., 1997) and may be generally useful to improve the furan tolerance in many microbial biocatalysts. Deletion of the chromosomal ucpA was detrimental for furfural tolerance, providing a clear phenotype for this cryptic gene.

TABLE 1

Bacterial strains, plasmids, and primers

| Strains, plasmids, or primers | Relevant characteristics | Reference of source |
|---|---|---|
| Strains | | |
| LY180 | ΔfrdBC::(Zm frg celY$_{Ec}$), ΔldhA::(Zm frg casAB$_{Ko}$), adhE::(Zm frg estZ$_{Pp}$ FRT), ΔackA::FRT, rrlE::(pdc adhA adhB FRT), ΔmgsA::FRT | (Miller et al., 2009a) |
| KJ122 | ΔldhA, ΔadhE, Δ(focA-pflB), ΔAackA, ΔmgsA, ΔpoxB, ΔsfcA, ΔaspC, ΔcitF, ΔtdcDE | (Jantama et al., 2008) |
| Plasmids | | |
| pTrc99A | Ptrc bla oriR rrnB lacI$^q$ | (Amann et al., 1988) |
| pLOI4317 | xdhABC in pTrc99A | This study |
| pLOI4320 | aldA in pTrc99A | This study |
| pLOI4855 | yeiTA in pTrc99A | This study |
| pLOI4856 | ucpA in pTrc99A | This study |
| Primers | | |
| | xdhABC cloning into SmaI-BamHI site | |
| xdhABC for | GCGCGCCCCGGGTATGGAAGCGCGGGAAGCAA (SEQ ID NO: 3) | This study |
| xdhABC rev | GCGCGCGGATCCCGGCATTGCTACGCTCTATC (SEQ ID NO: 4) | This study |
| | aldA cloning into EcoRI-HindIII site | |
| aldA for | CGCGCGGAATTCATAAATCACAGGAGTCGCCC (SEQ ID NO: 5) | This study |
| aldA rev | CGCGCGAAGCTTTCGCCTGGTACGATAACGAA (SEQ ID NO: 6) | This study |
| | yeiTA cloning into EcoR-Hind III site | |
| yeiTA for | GGAATTCCTTAATTACTCATAGCATTAAGGAAGATCACAT (SEQ ID NO: 7) | This study |
| yeiTA rev | GCGAAGCTTGTAATTATTTTTACCGTCATCAACTATGG (SEQ ID NO: 8) | This study |
| | ucpA cloning into EcoRI-Hind III site | |
| ucpA for | GGAATTCACGCTCTGTATTAACAAGGA (SEQ ID NO: 9) | This study |
| ucpA rev | AGCCAAGCTTCGGACGTGAAAGGAGTAACG (SEQ ID NO: 10) | This study |

TABLE 2

Known and putative oxidoreductase genes induces 3-fold or more by the addition of 1.5 g/liter furfural. Oxidoreductases with at least a 2 fold mRNA increase upon 1.5 g/L furfural addition in LY180

| Gene designation (b number) | Gene name | Fold increase | Predicted and/or tested Co-factor |
|---|---|---|---|
| b0283-b0286 | yagQRST | 2.2, 2.3, 4.7, 3.5 | FADH |
| b0306 | ykgE | 2.0 | Unknown |
| b0355-b0356 | frmBA | 4.4, 5.7 | NADPH |
| b0419 | yajO | 2.6 | NADPH |
| b0599 | ybdH | 3.0 | Unknown |
| b0723-b0724 | sdhAB | 5.3, 5.8 | Ubiquinone |
| b0801 | ybiC | 2.2 | Unknown |
| b1004 | wrbA | 3.0 | NADPH |
| b1287 | yciW | 2.4 | Unknown |
| b1406 | ydbC | 2.9 | NADH or NADPH |
| b1415 | aldA | 4.2 | NADH |
| b1444 | ydcW | 2.5 | NADH |
| b1449 | yncB | 2.6 | NADH or NADPH |
| b1650 | nemA | 6.4 | FMN |
| b2137 | yobF | 8.5 | NADPH |
| b2146-b2147 | yeiTA | 3.1, 3.0 | NADH |
| b2172 | yeiQ | 2.3 | NADH |
| b2426 | ucpA | 4.5 | NADH or NADPH |
| b2545 | yphC | 2.3 | NADH or NADPH |
| b2799 | fucO | 4.4 | NADH |
| b2868 | xdhABC | 5.8 | NADH |
| b2886 | ygfS | 2.1 | Unknown |
| b2899 | yqfA | 2.2 | Unknown |
| b3001 | yghZ | 2.0 | NADPH |
| b3011 | yqhD | 4.6 | NADPH |
| b3012 | dkgA | 5.4 | NADPH |
| b3572 | yiaK | 2.4 | NADH |
| b3588 | aldB | 5.7 | NADP+ |

TABLE 3

Summary of pH-controlled fermentations (10% xylose)[a]

| Strains | Furfural (mM) | Furfural-dependent slow growth μ (h⁻¹) | Duration (h)[b] | μ Max (h⁻¹) | Cell Yield (g L⁻¹) |
|---|---|---|---|---|---|
| LY180/pTrc99A | 0 | No slow phase | | 0.23 ± 0.1 | 4.6 ± 0.1 |
| LY180/pTrc99A | 10 | <0.04 | >72 | <0.04 | 0.06 ± 0.01 |
| LY180/pLOI4856 | 0 | No slow phase | | 0.22 ± 0.01 | 4.5 ± 0.2 |
| LY180/pLOI4856 | 10 | 0.09 ± 0.01 | 22 ± 2 | 0.14 ± 0.01 | 3.6 ± 0.1 |
| LY180 | 0 | No slow phase | | 0.23 ± 0.01 | 3.6 ± 0.2 |
| LY180 | 8 | 0.09 ± 0.01 | 21 ± 1 | 0.16 ± 0.01 | 4.0 ± 0.1 |
| LY180 | 10 | <0.04 | >72 | <0.04 | 0.08 ± 0.02 |
| XW118[c] | 0 | No slow phase | | 0.22 ± 0.03 | 3.1 ± 0.2 |
| XW118 | 8 | 0.01 ± 0.01 | 55 ± 2 | 0.14 ± 0.01 | 4.0 ± 0.1 |
| XW118 | 10 | <0.04 | >72 | <0.04 | 0.04 ± 0.01 |
| E. coli W | 0 | No slow phase | | 0.23 ± 0.01 | 2.0 ± 0.1 |
| E. coli W | 8 | 0.18 ± 0.01 | 13 ± 1 | 0.19 ± 0.01 | 1.9 ± 0.1 |
| E. coli W | 10 | 0.06 ± 0.02 | 21 ± 1 | 0.20 ± 0.02 | 2.0 ± 0.1 |
| XW137[d] | 0 | No slow phase | | 0.22 ± 0.01 | 2.0 ± 0.1 |
| XW137 | 8 | 0.11 ± 0.02 | 16 ± 3 | 0.19 ± 0.01 | 1.9 ± 0.1 |
| XW137 | 10 | 0.02 ± 0.01 | 37 ± 2 | 0.12 ± 0.02 | 1.9 ± 0.1 |
| E. coli W/pTrc99A | 0 | No slow phase | | 0.23 ± 0.01 | 2.4 ± 0.2 |
| E. coli W/pTrc99A | 10 | 0.03 ± 0.01 | 26 ± 4 | 0.13 ± 0.01 | 2.0 ± 0.3 |
| E. coli W/pLOI4856 | 0 | No slow phase | | 0.22 ± 0.01 | 1.9 ± 0.1 |
| E. coli W/pLOI4856 | 10 | 0.07 ± 0.01 | 16 ± 2 | 0.18 ± 0.02 | 2.5 ± 0.3 |

[a]Fermentations (n = 2; n = 4) were performed in AM1 medium with 100 g xylose liter⁻¹ (Wang et al., 2011b).
[b]The duration of furfural-induced slow growth was estimated as the time of intersection using extrapolated rates.
[c]XW118 (LY180 ucpA::kan)
[d]XW137 (E. coli W ucpA::kan)

REFERENCES

Almeida, J. R., M. Bertilsson, M. F. Gorwa-Grauslund, S. Gorsich, and G. Liden. 2009. Metabolic effects of furaldehydes and impacts on biotechnological processes. Appl. Microbiol. Biotechnol. 82:625-638.

Almeida, J. R., A. Roder, T. Modig, B. Laadan, G. Liden, and M. F. Gorwa-Grauslund. 2008. NADH- vs NADPH-coupled reduction of 5-hydroxymethyl furfural (HMF) and its implications on product distribution in *Saccharomyces cerevisiae*. Appl. Microbiol. Biotechnol. 78:939-945.

Alvira, P., E. Tomas-Pejo, M. Ballesteros, and M. J. Negro. 2010. Pretreatment technologies for an efficient bioethanol production process based on enzymatic hydrolysis: A review. Bioresour. Technol. 101:4851-4861.

Amann, E., B. Ochs, and K. J. Abel. 1988. Tightly regulated tac promoter vectors useful for the expression of unfused and fused proteins in *Escherichia coli*. Gene 69:301-315.

Carole, T. M., J. Pellegrino, and M. D. Paster. 2004. Opportunities in the industrial biobased products industry. Appl. Biochem. Biotechnol. 113-116:871-885.

Frick, O., and C. Wittmann. 2005. Characterization of the metabolic shift between oxidative and fermentative growth in *Saccharomyces cerevisiae* by comparative 13C flux analysis. Microb. Cell. Fact. 4:30.

Geddes, C. C., M. T. Mullinnix, I. U. Nieves, J. J. Peterson, R. W. Hoffman, S. W. York, L. P. Yomano, E. N. Miller, K. T. Shanmugam, and L. O. Ingram. 2010a. Simplified process for ethanol production from sugarcane bagasse using hydrolysate-resistant *Escherichia coli* strain MM160. Bioresour. Technol. 102:2702-2711.

Geddes, C. C., J. J. Peterson, C. Roslander, G. Zacchi, M. T. Mullinnix, K. T. Shanmugam, and L. O. Ingram. 2010b. Optimizing the saccharification of sugar cane bagasse using dilute phosphoric acid followed by fungal cellulases. Bioresour. Technol. 101:1851-1857.

Guo, K., P. Lukacik, E. Papagrigoriou, M. Meier, W. H. Lee, J. Adamski, and U. Oppermann. 2006. Characterization of human DHRS6, an orphan short chain dehydrogenase/reductase enzyme: a novel, cytosolic type 2 R-beta-hydroxybutyrate dehydrogenase. J. Biol. Chem. 281:10291-10297.

Grabowska, D., and A. Chelstowska. 2003. The ALD6 gene product is indispensable for providing NADPH in yeast cells lacking glucose-6-phosphate dehydrogenase activity. J. Biol. Chem. 278:13984-13988.

Jantama, K., X. Zhang, J. C. Moore, K. T. Shanmugam, and L. O. Ingram. 2008. Eliminating side products and increasing succinate yields in engineered strains of *Escherichia coli*. C. Biotechnol. Bioengin. 101:881-893.

Jarboe, L. R., T. B. Grabar, L. P. Yomano, K. T. Shanmugan, and L. O. Ingram. 2007. Development of ethanologenic bacteria. Adv. Biochem. Eng Biotechnol. 108:237-261.

Jarboe, L. R., X. Zhang, X. Wang, J. C. Moore, K. T. Shanmugam, and L. O. Ingram. 2010. Metabolic engineering for production of biorenewable fuels and chemicals: contributions of synthetic biology. J. Biomed. Biotechnol. 2010:761042.

Laadan, B., J. R. Almeida, P. Radstrom, B. Hahn-Hagerdal, and M. Gorwa-Grauslund. 2008. Identification of an NADH-dependent 5-hydroxymethylfurfural-reducing alcohol dehydrogenase in *Saccharomyces cerevisiae*. Yeast 25:191-198.

Liu, Z. L. 2006. Genomic adaptation of ethanologenic yeast to biomass conversion inhibitors. Appl. Microbiol. Biotechnol. 73:27-36.

Liu, Z. L., and J. Moon. 2009. A novel NADPH-dependent aldehyde reductase gene from *Saccharomyces cerevisiae* NRRL Y-12632 involved in the detoxification of aldehyde inhibitors derived from lignocellulosic biomass conversion. Gene 446:1-10.

Liu, Z. L., J. Moon, B. J. Andersh, P. J. Slininger, and S. Weber. 2008. Multiple gene-mediated NAD(P)H-dependent aldehyde reduction is a mechanism of in situ detoxification of furfural and 5-hydroxymethylfurfural by *Saccharomyces cerevisiae*. Appl. Microbiol. Biotechnol. 81:743-753.

Martinez, A., M. E. Rodriguez, M. L. Wells, S. W. York, J. F. Preston, and L. O. Ingram. 2001. Detoxification of dilute acid hydrolysates of lignocellulose with lime. Biotechnol. Prog. 17:287-293.

Martinez, A., M. E. Rodriguez, S. W. York, J. F. Preston, and L. O. Ingram. 2000a. Effects of Ca(OH)(2) treatments ("overliming") on the composition and toxicity of bagasse hemicellulose hydrolysates. Biotechnol. Bioeng. 69:526-536.

Martinez, A., M. E. Rodriguez, S. W. York, J. F. Preston, and L. O. Ingram. 2000b. Use of UV absorbance to monitor furans in dilute acid hydrolysates of biomass. Biotechnol. Prog. 16:637-641.

Miller, E. N., L. R. Jarboe, P. C. Turner, P. Pharkya, L. P. Yomano, S. W. York, D. Nunn, K. T. Shanmugam, and L. O. Ingram. 2009a. Furfural inhibits growth by limiting sulfur assimilation in ethanologenic *Escherichia coli* strain LY180. Appl. Environ. Microbiol. 75:6132-6141.

Miller, E. N., L. R. Jarboe, L. P. Yomano, S. W. York, K. T. Shanmugam, and L. O. Ingram. 2009b. Silencing of NADPH-dependent oxidoreductase genes (yqhD and dkgA) in furfural-resistant ethanologenic *Escherichia coli*. Appl. Environ. Microbiol. 75:4315-4323.

Miller, E. N., P. C. Turner, L. R. Jarboe, and L. O. Ingram. 2010. Genetic changes that increase 5-hydroxymethyl furfural resistance in ethanol-producing *Escherichia coli* LY180. Biotechnol. Lett. 32:661-667.

Mills, T. Y., N. R. Sandoval, and R. T. Gill. 2009. Cellulosic hydrolysate toxicity and tolerance mechanisms in *Escherichia coli*. Biotechnol. Biofuels. 2:26.

Park, S. M., A. J. Sinskey, and G. Stephanopoulos. 1997. Metabolic and physiological studies of *Corynebacterium glutamicum* mutants. Biotechnol Bioeng. 55:864-879.

Saha, B. C. 2003. Hemicellulose bioconversion. J. Ind. Microbiol. Biotechnol. 30:279-291.

Sauer, U., F. Canonaco, S. Heri, A. Perrenoud, E. Fischer. 2004. The soluble and membrane-bound transhydrogenases UdhA and PntAB have divergent functions in NADPH metabolism of *Escherichia coli*. J Biol Chem. 279:6613-6619.

Sirko, A., A. Weglenska, M. Hryniewicz, and D. M. Hulanicka. 1997. Characterization of the *Escherichia coli* gene encoding a new member of the short-chain dehydrogenase/ reductase (SDR) family. Acta Biochim Pol. 44:153-157.

Turner, P. C., E. N. Miller, L. R. Jarboe, C. L. Baggett, K. T. Shanmugam, and L. O. Ingram. 2010. YqhC regulates transcription of the adjacent *Escherichia coli* genes yqhD and dkgA that are involved in furfural tolerance. J. Ind. Microbiol. Biotechnol. doi:10.1007/s10295-010-0787-5.

Wang, X., E. N. Miller, L. P. Yomano, X. Zhang, K. T. Shanmugam and L. O. Ingram. 2011a. Overexpression of NADH-dependent oxidoreductase fucO increases furfural tolerance in *Escherichia coli* strains engineered for the production of ethanol and lactate. Appl. Environ. Microbiol. Accepted for Publication.

Wang, X., E. N. Miller, L. P. Yomano, X. Zhang, K. T. Shanmugam and L. O. Ingram. 2011b. Increased furfural tolerance due to overexpression of NADH-dependent oxidoreductase FucO in *Escherichia coli* strains engineered for the production of ethanol and lactate. Appl. Environ. Microbiol. 77:5132-5140.

Zaldivar, J., A. Martinez, and L. O. Ingram. 2000. Effect of alcohol compounds found in hemicellulose hydrolysate on the growth and fermentation of ethanologenic *Escherichia coli*. Biotechnol. Bioeng. 68:524-530.

Zaldivar, J., A. Martinez, and L. O. Ingram. 1999. Effect of selected aldehydes on the growth and fermentation of ethanologenic *Escherichia coli*. Biotechnol. Bioeng. 65:24-33.

Zhang, Xueli, K. Jantama, J. C. Moore, L. R. Jarboe, K. T. Shanmugam, and L. O. Ingram. 2009. Metabolic evolution of energy-conserving pathways for succinate production in *Escherichia coli*. Proc. Natl. Acad. Sci. U.S.A 106: 20180-20185.

We claim:

1. An isolated bacterial, fungal or yeast cell having increased UcpA activity as compared to a reference bacterial, fungal or yeast cell, wherein said bacterial, fungal or yeast cell having increased UcpA activity exhibits increased tolerance to furfural and/or 5-hydroxymethylfurfural (5-HMF), wherein said bacterial, fungal or yeast cell expresses increased amounts of a UcpA polypeptide comprising SEQ ID NO: 1.

2. The isolated bacterial, fungal or yeast cell of claim 1, wherein said bacterial, fungal or yeast cell produces a desired product or has been genetically engineered to produce a desired product selected from the group consisting of ethanol, lactic acid, succinic acid, malic acid, acetic acid, 1,3-propanediol, 2,3-propanediol, 1,4-butanediol, 2,3-butanediol, butanol, pyruvate, dicarboxylic acids, adipic acid and amino acids.

3. The isolated bacterial, fungal or yeast cell of claim 2, wherein said bacterial, fungal or yeast cell exhibits increased production of said desired product as compared to a reference bacterial, fungal or yeast cell in the presence of furfural and/or 5-hydroxymethylfurfural (5-HMF).

4. The isolated bacterial cell of claim 3, wherein:
   a) expression of the yqhD gene is reduced in said bacterial cell as compared to a reference bacterial cell;
   b) expression of the dkgA gene is reduced in said bacterial cell as compared to a reference bacterial cell;
   c) expression of the yqhD gene, yqhC gene and/or the dkgA gene are reduced in said bacterial cell as compared to expression in a reference bacterial cell;
   d) expression of the yqhC gene is reduced in said bacterial cell as compared to expression in a reference bacterial cell;
   e) expression of the yqhD gene, the yqhC gene and the dkgA genes is reduced in said bacterial cell as compared to expression in a reference bacterial cell;
   f) the yqhD gene is not expressed or is deleted in said bacterial cell;
   g) the yqhD gene and the dkgA gene are not expressed or are deleted in said bacterial cell;
   h) the yqhC gene or yqhD gene, the yqhC gene and the dkgA gene are not expressed or are deleted in said bacterial cell;
   i) the yqhC gene is not expressed or is deleted in said bacterial cell;
   j) the dkgA gene is not expressed in said bacterial cell;
   k) the activity of the yqhD gene, yqhC gene and/or the dkgA gene product(s) are reduced in said bacterial cell as compared to expression in a reference bacterial cell; or
   l) the activity of the yqhC gene product is reduced in said bacterial cell as compared to expression in a reference bacterial cell.

5. The isolated bacterial, fungal or yeast cell of claim 1, wherein said bacterial, fungal or yeast cell further exhibits increased FucO activity, said FucO activity being increased by:
   a) expressing the FucO gene in a plasmid or a multicopy plasmid with a native promoter or a promoter sequence;
   b) integration of additional copies of the FucO gene within the chromosome of a bacterial, fungal or yeast cell;
   c) replacement of the FucO gene native promoter with a promoter that increases the level of gene expression in a bacterial cell; or
   d) the FucO enzyme is mutated to increase catalytic efficiency or reduce its Km.

6. The isolated bacterial, fungal or yeast cell of claim 1, wherein said bacterial, fungal or yeast cell expresses increased amounts of mRNA encoding the UcpA polypeptide comprising SEQ ID NO: 1.

7. A method of growing a bacterial, fungal or yeast cell comprising culturing a bacterial, fungal or yeast cell according to claim 1 under conditions that allow for the growth of said bacterial, fungal or yeast cell.

8. The method of claim 7, wherein the bacterial, fungal or yeast cell produces a desired product, or has been genetically engineered to produce a desired product, selected from the group consisting of ethanol, lactic acid, succinic acid, malic acid, acetic acid, 1,3-propanediol, 2,3-propanediol, 1,4-butanediol, 2,3-butanediol, butanol, pyruvate, dicarboxylic acids, adipic acid and amino acids.

9. A method for producing a desired product from a biomass, a hemicellulosic biomass, a lignocellulosic biomass, a cellulosic biomass or an oligosaccharide source comprising contacting the biomass, hemicellulosic biomass, lignocellulosic biomass, cellulosic biomass or oligosaccharide with the isolated bacterial, fungal or yeast cell according to claim 1 and producing said desired product by fermenting said biomass, a hemicellulosic biomass, a lignocellulosic biomass, a cellulosic biomass or an oligosaccharide source in the presence of said bacterial, fungal or yeast cell.

10. The method of claim 9, wherein the bacterial, fungal or yeast cell produces a desired product, or has been genetically engineered to produce a desired product, selected from the group consisting of ethanol, lactic acid, succinic acid, malic acid, acetic acid, 1,3-propanediol, 2,3-propanediol, 1,4-butanediol, 2,3-butanediol, butanol, pyruvate, dicarboxylic acids, adipic acid and amino acids.

11. A method of increasing furfural and/or 5-hydroxymethylfurfural (5-HMF) resistance in a bacterial, fungal or yeast cell comprising increasing UcpA activity in said bacterial, fungal or yeast cell, as compared to a reference bacterial, fungal or yeast cell, wherein said bacterial, fungal or yeast cell having increased UcpA activity increases resistance of said bacterial, fungal or yeast cell to furfural and/or 5-hydroxymethylfurfural (5-HMF), and wherein said bacterial, fungal or yeast cell expresses increased amounts of a UcpA polypeptide comprising SEQ ID NO: 1.

12. The method of claim 11, further comprising increasing FucO activity in said bacterial, fungal or yeast cell, said FucO activity being increased by:
  a) expressing the FucO gene in a plasmid or a multicopy plasmid with a native promoter or a promoter sequence;
  b) transposon integration of additional copies of the FucO gene within the chromosome of a bacterial, fungal or yeast cell;
  c) replacement of the FucO gene native promoter with a promoter that increases the level of gene expression in a bacterial, fungal or yeast cell; or
  d) the FucO enzyme is mutated to increase catalytic efficiency or reduce its Km.

\* \* \* \* \*